(12) United States Patent
Reicher et al.

(10) Patent No.: US 9,934,568 B2
(45) Date of Patent: *Apr. 3, 2018

(54) COMPUTER-AIDED ANALYSIS AND RENDERING OF MEDICAL IMAGES USING USER-DEFINED RULES

(71) Applicant: D.R. Systems, Inc., San Diego, CA (US)

(72) Inventors: Murray A. Reicher, Rancho Santa Fe, CA (US); Michael Trambert, Santa Barbara, CA (US); Evan K. Fram, Paradise Valley, AZ (US)

(73) Assignee: D.R. Systems, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/469,296

(22) Filed: Mar. 24, 2017

(65) Prior Publication Data
US 2017/0200270 A1    Jul. 13, 2017

Related U.S. Application Data

(63) Continuation-in-part of application No. 15/292,023, filed on Oct. 12, 2016, now Pat. No. 9,684,762, which
(Continued)

(51) Int. Cl.
*G06K 9/00* (2006.01)
*G06T 7/00* (2017.01)
(Continued)

(52) U.S. Cl.
CPC .......... *G06T 7/0012* (2013.01); *A61B 5/7271* (2013.01); *A61B 5/742* (2013.01);
(Continued)

(58) Field of Classification Search
None
See application file for complete search history.

(56) References Cited

U.S. PATENT DOCUMENTS 4,672,683 A    6/1987    Matsueda
5,123,056 A    6/1992    Wilson
(Continued)

FOREIGN PATENT DOCUMENTS

WO    WO 2007/131157    11/2007

OTHER PUBLICATIONS

US 7,801,341, 09/2010, Fram et al. (withdrawn)
(Continued)

*Primary Examiner* — Tahmina Ansari
(74) *Attorney, Agent, or Firm* — Knobbe Martens Olson & Bear LLP

(57) ABSTRACT

Systems and methods that allow transfer and display rules to be defined based on one or more of several attributes, such as a particular user, site, device, and/or image/series characteristic, as well as whether individual images and/or image series are classified as thin slices and/or based on other characteristics, and applied to medical images in order to determine which images and/or image data are analyzed, downloaded, viewed, stored, rendered, processed, and/or any number of other actions that might be performed with respect to medical image data. The system and methods may include image analysis, image rendering, image transformation, image enhancement, and/or other aspects to enable efficient and customized review of medical images.

20 Claims, 10 Drawing Sheets

Related U.S. Application Data is a continuation of application No. 15/163,600, filed on May 24, 2016, now Pat. No. 9,501,617, which is a continuation of application No. 14/687,853, filed on Apr. 15, 2015, now Pat. No. 9,386,084, which is a continuation of application No. 14/179,328, filed on Feb. 12, 2014, now Pat. No. 9,042,617, which is a continuation of application No. 12/891,543, filed on Sep. 27, 2010, now Pat. No. 8,712,120.

(60) Provisional application No. 61/246,479, filed on Sep. 28, 2009.

(51) Int. Cl.
| | |
|---|---|
| *G06T 11/60* | (2006.01) |
| *A61B 5/00* | (2006.01) |
| *H04L 29/06* | (2006.01) |
| *G06F 19/00* | (2018.01) |
| *G06T 15/08* | (2011.01) |
| *H04L 29/08* | (2006.01) |
| *G06T 15/00* | (2011.01) |

(52) U.S. Cl.
CPC ............ *G06F 19/321* (2013.01); *G06T 11/60* (2013.01); *G06T 15/08* (2013.01); *H04L 67/02* (2013.01); *H04L 67/10* (2013.01); *H04L 67/42* (2013.01); *G06F 2101/00* (2013.01); *G06T 15/005* (2013.01); *G06T 2207/30004* (2013.01)

(56) References Cited

U.S. PATENT DOCUMENTS

| | | | |
|---|---|---|---|
| 5,172,419 A | 12/1992 | Manian | |
| 5,179,651 A | 1/1993 | Taaffe et al. | |
| 5,431,161 A | 7/1995 | Ryals et al. | |
| 5,452,416 A | 9/1995 | Hilton et al. | |
| 5,515,375 A * | 5/1996 | DeClerck | H04J 3/1688 370/335 |
| 5,542,003 A | 7/1996 | Wofford | |
| 5,734,915 A | 3/1998 | Roewer | |
| 5,740,267 A | 4/1998 | Echerer et al. | |
| 5,779,634 A | 7/1998 | Ema et al. | |
| 5,807,256 A | 9/1998 | Taguchi | |
| 5,835,030 A * | 11/1998 | Tsutsui | G11B 20/00007 341/106 |
| 5,852,646 A | 12/1998 | Klotz et al. | |
| 5,857,030 A | 1/1999 | Gaborski | |
| 5,926,568 A | 7/1999 | Chaney et al. | |
| 5,954,650 A | 9/1999 | Saito et al. | |
| 5,976,088 A | 11/1999 | Urbano et al. | |
| 5,986,662 A | 11/1999 | Argiro et al. | |
| 5,987,345 A | 11/1999 | Engelmann et al. | |
| 5,995,644 A | 11/1999 | Lai et al. | |
| 6,008,813 A | 12/1999 | Lauer et al. | |
| 6,115,486 A | 9/2000 | Cantoni | |
| 6,128,002 A | 10/2000 | Leiper | |
| 6,130,671 A | 10/2000 | Argiro | |
| 6,151,581 A | 11/2000 | Kraftson et al. | |
| 6,175,643 B1 | 1/2001 | Lai et al. | |
| 6,177,937 B1 | 1/2001 | Stockham et al. | |
| 6,185,320 B1 | 2/2001 | Bick et al. | |
| 6,211,884 B1 | 4/2001 | Knittel et al. | |
| 6,219,059 B1 | 4/2001 | Argiro | |
| 6,219,061 B1 | 4/2001 | Lauer et al. | |
| 6,243,095 B1 | 6/2001 | Shile et al. | |
| 6,243,098 B1 | 6/2001 | Lauer et al. | |
| 6,262,740 B1 | 7/2001 | Lauer et al. | |
| 6,266,733 B1 | 7/2001 | Knittel et al. | |
| 6,269,379 B1 | 7/2001 | Hiyama et al. | |
| 6,297,799 B1 | 10/2001 | Knittel et al. | |
| 6,304,667 B1 | 10/2001 | Reitano | |
| 6,310,620 B1 | 10/2001 | Lauer et al. | |
| 6,313,841 B1 | 11/2001 | Ogata et al. | |
| 6,342,885 B1 | 1/2002 | Knittel et al. | |
| 6,347,329 B1 | 2/2002 | Evans | |
| 6,351,547 B1 | 2/2002 | Johnson et al. | |
| 6,356,265 B1 | 3/2002 | Knittel et al. | |
| 6,369,816 B1 | 4/2002 | Knittel et al. | |
| 6,383,135 B1 | 5/2002 | Chikovani et al. | |
| 6,388,687 B1 | 5/2002 | Brackett et al. | |
| 6,404,429 B1 | 6/2002 | Knittel | |
| 6,407,737 B1 | 6/2002 | Zhao et al. | |
| 6,411,296 B1 | 6/2002 | Knittel et al. | |
| 6,421,057 B1 | 7/2002 | Lauer et al. | |
| 6,424,346 B1 | 7/2002 | Correll et al. | |
| 6,424,996 B1 | 7/2002 | Killcommons et al. | |
| 6,426,749 B1 | 7/2002 | Knittel et al. | |
| 6,427,022 B1 | 7/2002 | Craine et al. | |
| 6,438,533 B1 | 8/2002 | Spackman et al. | |
| 6,463,169 B1 | 10/2002 | Ino et al. | |
| 6,476,810 B1 | 11/2002 | Simha et al. | |
| 6,512,517 B1 | 1/2003 | Knittel et al. | |
| 6,532,299 B1 | 3/2003 | Sachdeva et al. | |
| 6,532,311 B1 | 3/2003 | Pritt | |
| 6,556,695 B1 | 4/2003 | Packer et al. | |
| 6,556,724 B1 | 4/2003 | Chang et al. | |
| 6,563,950 B1 | 5/2003 | Wiskott et al. | |
| 6,574,629 B1 | 6/2003 | Cooke, Jr. et al. | |
| 6,577,753 B2 | 6/2003 | Ogawa | |
| 6,603,494 B1 | 8/2003 | Banks et al. | |
| 6,606,171 B1 | 8/2003 | Renk et al. | |
| 6,614,447 B1 | 9/2003 | Bhatia et al. | |
| 6,618,060 B1 | 9/2003 | Brackett | |
| 6,621,918 B1 | 9/2003 | Hu et al. | |
| 6,630,937 B2 | 10/2003 | Kallergi et al. | |
| 6,650,766 B1 | 11/2003 | Rogers | |
| 6,654,012 B1 | 11/2003 | Lauer et al. | |
| 6,678,764 B2 | 1/2004 | Parvelescu et al. | |
| 6,680,735 B1 | 1/2004 | Seiler et al. | |
| 6,683,933 B2 | 1/2004 | Saito et al. | |
| 6,697,067 B1 | 2/2004 | Callahan et al. | |
| 6,697,506 B1 | 2/2004 | Qian et al. | |
| 6,734,880 B2 | 5/2004 | Chang et al. | |
| 6,760,755 B1 * | 7/2004 | Brackett | H04L 29/06 709/214 |
| 6,775,402 B2 | 8/2004 | Bacus et al. | |
| 6,778,689 B1 | 8/2004 | Aksit et al. | |
| 6,820,093 B2 | 11/2004 | de la Huerga | |
| 6,820,100 B2 | 11/2004 | Funahashi | |
| 6,826,297 B2 | 11/2004 | Saito et al. | |
| 6,829,377 B2 | 12/2004 | Milioto | |
| 6,864,794 B2 | 3/2005 | Betz | |
| 6,886,133 B2 | 4/2005 | Bailey et al. | |
| 6,891,920 B1 | 5/2005 | Minyard et al. | |
| 6,894,707 B2 | 5/2005 | Nemoto | |
| 6,909,436 B1 | 6/2005 | Pianykh et al. | |
| 6,909,795 B2 | 6/2005 | Tecotzky et al. | |
| 6,917,696 B2 | 7/2005 | Soenksen | |
| 6,988,075 B1 | 1/2006 | Hacker | |
| 6,996,205 B2 | 2/2006 | Capolunghi et al. | |
| 7,016,952 B2 | 3/2006 | Mullen et al. | |
| 7,022,073 B2 | 4/2006 | Fan et al. | |
| 7,027,633 B2 | 4/2006 | Foran et al. | |
| 7,031,504 B1 | 4/2006 | Argiro et al. | |
| 7,031,846 B2 | 4/2006 | Kaushikkar et al. | |
| 7,039,723 B2 | 5/2006 | Hu et al. | |
| 7,043,474 B2 | 5/2006 | Mojsilovic | |
| 7,050,620 B2 | 5/2006 | Heckman | |
| 7,054,473 B1 | 5/2006 | Roehrig et al. | |
| 7,058,901 B1 | 6/2006 | Hafey et al. | |
| 7,092,572 B2 | 8/2006 | Huang et al. | |
| 7,103,205 B2 * | 9/2006 | Wang | A61B 6/463 382/132 |
| 7,106,479 B2 | 9/2006 | Roy et al. | |
| 7,110,616 B2 | 9/2006 | Ditt et al. | |
| 7,113,186 B2 | 9/2006 | Kim et al. | |
| 7,136,064 B2 | 11/2006 | Zuiderveld | |
| 7,139,416 B2 | 11/2006 | Vuylsteke | |
| 7,149,334 B2 | 12/2006 | Dehmeshki | |
| 7,155,043 B2 | 12/2006 | Daw | |
| 7,162,623 B2 | 1/2007 | Yngvesson | |
| 7,170,532 B2 | 1/2007 | Sako | |

(56) References Cited

U.S. PATENT DOCUMENTS

| | | |
|---|---|---|
| 7,174,054 B2 | 2/2007 | Manber et al. |
| 7,209,149 B2 | 4/2007 | Jogo |
| 7,209,578 B2 | 4/2007 | Saito et al. |
| 7,212,661 B2 | 5/2007 | Samara et al. |
| 7,218,763 B2 | 5/2007 | Belykh et al. |
| 7,224,852 B2 | 5/2007 | Lipton et al. |
| 7,236,558 B2 | 6/2007 | Saito et al. |
| 7,260,249 B2 | 8/2007 | Smith |
| 7,263,710 B1 | 8/2007 | Hummel et al. |
| 7,272,610 B2 | 9/2007 | Torres |
| 7,346,199 B2 | 3/2008 | Pfaff |
| 7,366,992 B2 | 4/2008 | Thomas, III |
| 7,379,578 B2 | 5/2008 | Soussaline et al. |
| 7,412,111 B2 | 8/2008 | Battle et al. |
| 7,450,747 B2 | 11/2008 | Jabri et al. |
| 7,492,970 B2 | 2/2009 | Saito et al. |
| 7,505,782 B2 | 3/2009 | Chu |
| 7,516,417 B2 | 4/2009 | Amador et al. |
| 7,525,554 B2 | 4/2009 | Morita et al. |
| 7,526,114 B2 | 4/2009 | Xia et al. |
| 7,526,132 B2 | 4/2009 | Koenig |
| 7,545,965 B2 | 6/2009 | Suzuki et al. |
| 7,574,029 B2 | 8/2009 | Peterson et al. |
| 7,583,861 B2 | 9/2009 | Hanna et al. |
| 7,590,272 B2 | 9/2009 | Brejl et al. |
| 7,613,335 B2 | 11/2009 | McLennan et al. |
| 7,634,121 B2 | 12/2009 | Novatzky et al. |
| 7,636,413 B2 | 12/2009 | Toth |
| 7,639,879 B2 | 12/2009 | Goto et al. |
| 7,656,543 B2 | 2/2010 | Atkins |
| 7,660,481 B2 | 2/2010 | Schaap et al. |
| 7,660,488 B2 | 2/2010 | Reicher et al. |
| 7,668,352 B2 | 2/2010 | Tecotzky et al. |
| 7,683,909 B2 | 3/2010 | Takekoshi |
| 7,698,152 B2 | 4/2010 | Reid |
| 7,716,277 B2 | 5/2010 | Yamatake |
| 7,787,672 B2 | 8/2010 | Reicher et al. |
| 7,834,891 B2 | 11/2010 | Yarger et al. |
| 7,835,560 B2 | 11/2010 | Vining et al. |
| 7,885,440 B2 | 2/2011 | Fram et al. |
| 7,885,828 B2 | 2/2011 | Glaser-Seidnitzer et al. |
| 7,899,514 B1 | 3/2011 | Kirkland |
| 7,920,152 B2 | 4/2011 | Fram et al. |
| 7,953,614 B1 | 5/2011 | Reicher |
| 7,970,188 B2 | 6/2011 | Mahesh et al. |
| 7,970,625 B2 | 6/2011 | Reicher et al. |
| 7,991,210 B2 | 8/2011 | Peterson et al. |
| 7,992,100 B2 | 8/2011 | Lundstrom et al. |
| 8,019,138 B2 | 9/2011 | Reicher et al. |
| 8,046,044 B2 | 10/2011 | Stazzone et al. |
| 8,050,938 B1 | 11/2011 | Green, Jr. et al. |
| 8,065,166 B2 | 11/2011 | Maresh et al. |
| 8,073,225 B2 | 12/2011 | Hagen et al. |
| 8,094,901 B1 | 1/2012 | Reicher et al. |
| 8,150,708 B2 | 4/2012 | Kotula et al. |
| 8,214,756 B2 | 7/2012 | Salazar-Ferrer et al. |
| 8,217,966 B2 | 7/2012 | Fram et al. |
| 8,244,014 B2 | 8/2012 | Reicher et al. |
| 8,249,687 B2 | 8/2012 | Peterson et al. |
| 8,292,811 B2 | 10/2012 | Relkuntwar et al. |
| 8,370,293 B2 | 2/2013 | Iwase et al. |
| 8,379,051 B2 | 2/2013 | Brown |
| 8,380,533 B2 | 2/2013 | Reicher et al. |
| 8,391,643 B2 | 3/2013 | Melbourne et al. |
| 8,406,491 B2 | 3/2013 | Gee et al. |
| 8,457,990 B1 | 6/2013 | Reicher et al. |
| 8,554,576 B1 | 10/2013 | Reicher et al. |
| 8,560,050 B2 | 10/2013 | Martin et al. |
| 8,610,746 B2 | 12/2013 | Fram et al. |
| 8,626,527 B1 | 1/2014 | Reicher et al. |
| 8,693,757 B2 | 4/2014 | Gundel |
| 8,712,120 B1 | 4/2014 | Reicher et al. |
| 8,731,259 B2 | 5/2014 | Reicher et al. |
| 8,751,268 B1 | 6/2014 | Reicher et al. |
| 8,797,350 B2 | 8/2014 | Fram |
| 8,879,807 B2 | 11/2014 | Fram et al. |
| 8,913,808 B2 | 12/2014 | Reicher et al. |
| 9,042,617 B1 * | 5/2015 | Reicher .................. H04L 67/02 382/128 |
| 9,075,899 B1 | 7/2015 | Reicher |
| 9,092,551 B1 | 7/2015 | Reicher |
| 9,092,727 B1 | 7/2015 | Reicher |
| 9,324,188 B1 | 4/2016 | Fram et al. |
| 9,386,084 B1 | 7/2016 | Reicher et al. |
| 9,471,210 B1 | 10/2016 | Fram et al. |
| 9,495,604 B1 | 11/2016 | Fram |
| 9,501,617 B1 | 11/2016 | Reicher et al. |
| 9,501,627 B2 | 11/2016 | Reicher et al. |
| 9,501,863 B1 | 11/2016 | Fram et al. |
| 9,536,106 B2 | 1/2017 | Fram |
| 9,536,324 B1 | 1/2017 | Fram |
| 9,542,082 B1 | 1/2017 | Reicher et al. |
| 9,672,477 B1 | 6/2017 | Reicher et al. |
| 9,727,938 B1 | 8/2017 | Reicher et al. |
| 9,754,074 B1 | 9/2017 | Reicher et al. |
| 9,836,202 B1 | 12/2017 | Reicher et al. |
| 2001/0016822 A1 | 8/2001 | Bessette |
| 2001/0042124 A1 | 11/2001 | Barron |
| 2002/0016718 A1 | 2/2002 | Rothschild et al. |
| 2002/0021828 A1 | 2/2002 | Papier et al. |
| 2002/0039084 A1 | 4/2002 | Yamaguchi |
| 2002/0044696 A1 | 4/2002 | Sirohey et al. |
| 2002/0070970 A1 | 6/2002 | Wood et al. |
| 2002/0073429 A1 | 6/2002 | Beane et al. |
| 2002/0090118 A1 | 7/2002 | Olschewski |
| 2002/0090119 A1 | 7/2002 | Saito et al. |
| 2002/0090124 A1 | 7/2002 | Soubelet et al. |
| 2002/0091659 A1 | 7/2002 | Beaulieu et al. |
| 2002/0103673 A1 | 8/2002 | Atwood |
| 2002/0103827 A1 | 8/2002 | Sesek |
| 2002/0110285 A1 | 8/2002 | Wang et al. |
| 2002/0144697 A1 | 10/2002 | Betz |
| 2002/0172408 A1 | 11/2002 | Saito et al. |
| 2002/0172409 A1 | 11/2002 | Saito et al. |
| 2002/0180883 A1 | 12/2002 | Tomizawa et al. |
| 2002/0186820 A1 | 12/2002 | Saito et al. |
| 2002/0190984 A1 | 12/2002 | Seiler et al. |
| 2003/0005464 A1 | 1/2003 | Gropper et al. |
| 2003/0013951 A1 | 1/2003 | Stefanescu |
| 2003/0016850 A1 | 1/2003 | Kaufman et al. |
| 2003/0028402 A1 | 2/2003 | Ulrich et al. |
| 2003/0034973 A1 | 2/2003 | Zuiderveld |
| 2003/0037054 A1 | 2/2003 | Dutta et al. |
| 2003/0055896 A1 | 3/2003 | Hu et al. |
| 2003/0065613 A1 | 4/2003 | Smith |
| 2003/0071829 A1 | 4/2003 | Bodicker et al. |
| 2003/0101291 A1 | 5/2003 | Mussack et al. |
| 2003/0115083 A1 | 6/2003 | Masarie et al. |
| 2003/0120516 A1 | 6/2003 | Perednia |
| 2003/0130973 A1 | 7/2003 | Sumner, II et al. |
| 2003/0140141 A1 | 7/2003 | Mullen et al. |
| 2003/0156745 A1 | 8/2003 | Saito et al. |
| 2003/0160095 A1 | 8/2003 | Segal |
| 2003/0164860 A1 | 9/2003 | Shen et al. |
| 2003/0184778 A1 | 10/2003 | Chiba |
| 2003/0187689 A1 | 10/2003 | Barnes et al. |
| 2003/0190062 A1 | 10/2003 | Noro et al. |
| 2003/0204420 A1 | 10/2003 | Wilkes et al. |
| 2003/0215122 A1 | 11/2003 | Tanaka |
| 2004/0015703 A1 | 1/2004 | Madison et al. |
| 2004/0024303 A1 | 2/2004 | Banks et al. |
| 2004/0068170 A1 * | 4/2004 | Wang .................... A61B 6/463 600/407 |
| 2004/0086163 A1 | 5/2004 | Moriyama et al. |
| 2004/0088192 A1 | 5/2004 | Schmidt et al. |
| 2004/0105030 A1 | 6/2004 | Yamane |
| 2004/0105574 A1 | 6/2004 | Pfaff |
| 2004/0114714 A1 | 6/2004 | Minyard et al. |
| 2004/0122705 A1 | 6/2004 | Sabol et al. |
| 2004/0141661 A1 * | 7/2004 | Hanna .................. G06F 19/321 382/305 |
| 2004/0143582 A1 | 7/2004 | Vu |
| 2004/0161164 A1 | 8/2004 | Dewaele |
| 2004/0165791 A1 | 8/2004 | Kaltanji |

(56) References Cited

U.S. PATENT DOCUMENTS

| | | |
|---|---|---|
| 2004/0172306 A1 | 9/2004 | Wohl et al. |
| 2004/0174429 A1 | 9/2004 | Chu |
| 2004/0190780 A1 | 9/2004 | Shiibashi et al. |
| 2004/0202387 A1 | 10/2004 | Yngvesson |
| 2004/0243435 A1 | 12/2004 | Williams |
| 2004/0252871 A1 | 12/2004 | Tecotzky et al. |
| 2004/0254816 A1 | 12/2004 | Myers |
| 2004/0255252 A1 | 12/2004 | Rodriguez et al. |
| 2005/0010531 A1* | 1/2005 | Kushalnagar ........... G06F 21/10 705/59 |
| 2005/0027569 A1 | 2/2005 | Gollogly et al. |
| 2005/0027570 A1 | 2/2005 | Maier et al. |
| 2005/0043970 A1 | 2/2005 | Hsieh |
| 2005/0063575 A1 | 3/2005 | Ma et al. |
| 2005/0065424 A1 | 3/2005 | Shah et al. |
| 2005/0074150 A1 | 4/2005 | Bruss |
| 2005/0074157 A1 | 4/2005 | Thomas, III |
| 2005/0075544 A1 | 4/2005 | Shapiro et al. |
| 2005/0088534 A1 | 4/2005 | Shen et al. |
| 2005/0107689 A1 | 5/2005 | Sasano |
| 2005/0108058 A1 | 5/2005 | Weidner et al. |
| 2005/0110791 A1 | 5/2005 | Krishnamoorthy et al. |
| 2005/0111733 A1 | 5/2005 | Fors et al. |
| 2005/0113681 A1 | 5/2005 | DeFreitas et al. |
| 2005/0114178 A1 | 5/2005 | Krishnamurthy et al. |
| 2005/0114179 A1 | 5/2005 | Brackett et al. |
| 2005/0114283 A1 | 5/2005 | Pearson et al. |
| 2005/0143654 A1 | 6/2005 | Zuiderveld et al. |
| 2005/0171818 A1 | 8/2005 | McLaughlin |
| 2005/0184988 A1 | 8/2005 | Yanof et al. |
| 2005/0197860 A1 | 9/2005 | Joffe et al. |
| 2005/0238218 A1 | 10/2005 | Nakamura |
| 2005/0244041 A1 | 11/2005 | Tecotzky et al. |
| 2005/0251013 A1 | 11/2005 | Krishnan |
| 2005/0254729 A1 | 11/2005 | Saito et al. |
| 2005/0273009 A1 | 12/2005 | Deischinger et al. |
| 2006/0008181 A1 | 1/2006 | Takekoshi |
| 2006/0031097 A1 | 2/2006 | Lipscher et al. |
| 2006/0050152 A1 | 3/2006 | Rai et al. |
| 2006/0058603 A1* | 3/2006 | Dave ................. A61B 5/0476 600/407 |
| 2006/0061570 A1 | 3/2006 | Cheryauka et al. |
| 2006/0093207 A1* | 5/2006 | Reicher ................ G06F 19/321 382/156 |
| 2006/0095423 A1* | 5/2006 | Reicher ................ G06F 19/327 |
| 2006/0095426 A1 | 5/2006 | Takachio et al. |
| 2006/0111941 A1 | 5/2006 | Blom |
| 2006/0122482 A1 | 6/2006 | Mariotti et al. |
| 2006/0171574 A1 | 8/2006 | DelMonego et al. |
| 2006/0181548 A1 | 8/2006 | Hafey |
| 2006/0188134 A1 | 8/2006 | Quist |
| 2006/0230072 A1 | 10/2006 | Partovi et al. |
| 2006/0241979 A1* | 10/2006 | Sato ................. G06F 17/30265 705/3 |
| 2006/0267976 A1 | 11/2006 | Saito et al. |
| 2006/0274145 A1 | 12/2006 | Reiner |
| 2006/0276708 A1 | 12/2006 | Peterson et al. |
| 2006/0277075 A1 | 12/2006 | Salwan |
| 2006/0282408 A1 | 12/2006 | Wisely et al. |
| 2007/0009078 A1 | 1/2007 | Saito et al. |
| 2007/0021977 A1 | 1/2007 | Elsholz |
| 2007/0050701 A1 | 3/2007 | El Emam et al. |
| 2007/0055550 A1 | 3/2007 | Courtney et al. |
| 2007/0064984 A1 | 3/2007 | Vassa et al. |
| 2007/0067124 A1 | 3/2007 | Kimpe et al. |
| 2007/0073556 A1 | 3/2007 | Lau et al. |
| 2007/0106535 A1 | 5/2007 | Matsunaga |
| 2007/0106633 A1 | 5/2007 | Reiner |
| 2007/0109299 A1 | 5/2007 | Peterson |
| 2007/0109402 A1 | 5/2007 | Niwa |
| 2007/0110294 A1 | 5/2007 | Schaap et al. |
| 2007/0116345 A1 | 5/2007 | Peterson et al. |
| 2007/0116346 A1 | 5/2007 | Peterson et al. |
| 2007/0122016 A1 | 5/2007 | Brejl et al. |
| 2007/0124541 A1* | 5/2007 | Lang ................... G06F 12/0862 711/137 |
| 2007/0140536 A1 | 6/2007 | Sehnert |
| 2007/0159962 A1 | 7/2007 | Mathavu et al. |
| 2007/0162308 A1* | 7/2007 | Peters ................... G06F 19/322 705/2 |
| 2007/0165917 A1 | 7/2007 | Cao et al. |
| 2007/0174079 A1 | 7/2007 | Kraus |
| 2007/0192138 A1 | 8/2007 | Saito et al. |
| 2007/0192140 A1 | 8/2007 | Gropper |
| 2007/0237380 A1 | 10/2007 | Iwase et al. |
| 2007/0239481 A1 | 10/2007 | DiSilvestro et al. |
| 2008/0016111 A1 | 1/2008 | Keen |
| 2008/0021877 A1 | 1/2008 | Saito et al. |
| 2008/0059245 A1 | 3/2008 | Sakaida et al. |
| 2008/0100612 A1 | 5/2008 | Dastmalchi et al. |
| 2008/0103828 A1 | 5/2008 | Squilla et al. |
| 2008/0125846 A1 | 5/2008 | Battle et al. |
| 2008/0126982 A1 | 5/2008 | Sadikali et al. |
| 2008/0136838 A1 | 6/2008 | Goede et al. |
| 2008/0275913 A1 | 11/2008 | van Arragon et al. |
| 2008/0279439 A1 | 11/2008 | Minyard et al. |
| 2008/0300484 A1 | 12/2008 | Wang et al. |
| 2009/0005668 A1 | 1/2009 | West et al. |
| 2009/0022375 A1 | 1/2009 | Fidrich |
| 2009/0028410 A1 | 1/2009 | Shimazaki |
| 2009/0080719 A1 | 3/2009 | Watt |
| 2009/0091566 A1 | 4/2009 | Turney et al. |
| 2009/0123052 A1 | 5/2009 | Ruth et al. |
| 2009/0129643 A1* | 5/2009 | Natanzon ............. G06F 19/321 382/128 |
| 2009/0132586 A1 | 5/2009 | Napora et al. |
| 2009/0150481 A1* | 6/2009 | Garcia ................ H04L 12/2812 709/203 |
| 2009/0182577 A1 | 7/2009 | Squilla et al. |
| 2009/0198514 A1 | 8/2009 | Rhodes |
| 2009/0213034 A1 | 8/2009 | Wu et al. |
| 2009/0248442 A1 | 10/2009 | Pacheco et al. |
| 2009/0268986 A1 | 10/2009 | Holstein et al. |
| 2009/0326373 A1 | 12/2009 | Boese et al. |
| 2010/0053353 A1 | 3/2010 | Hunter et al. |
| 2010/0086182 A1 | 4/2010 | Hui |
| 2010/0131887 A1 | 5/2010 | Salazar-Ferrer et al. |
| 2010/0198608 A1 | 8/2010 | Kaboff et al. |
| 2010/0211409 A1 | 8/2010 | Kotula et al. |
| 2010/0246981 A1 | 9/2010 | Hu et al. |
| 2010/0299157 A1 | 11/2010 | Fram et al. |
| 2011/0110572 A1 | 5/2011 | Guehring et al. |
| 2011/0293162 A1 | 12/2011 | Pajeau |
| 2011/0316873 A1 | 12/2011 | Reicher |
| 2012/0070048 A1 | 3/2012 | Van Den Brink |
| 2012/0130729 A1 | 5/2012 | Raizada et al. |
| 2012/0136794 A1* | 5/2012 | Kushalnagar ........... G06F 21/10 705/59 |
| 2012/0163684 A1* | 6/2012 | Natanzon ............. G06F 19/321 382/128 |
| 2012/0284657 A1 | 11/2012 | Hafey et al. |
| 2013/0070998 A1 | 3/2013 | Shibata |
| 2013/0076681 A1 | 3/2013 | Sirpal et al. |
| 2013/0297331 A1 | 11/2013 | Zuehlsdorff et al. |
| 2014/0022194 A1 | 1/2014 | Ito |
| 2014/0142983 A1 | 5/2014 | Backhaus et al. |
| 2015/0160848 A1 | 6/2015 | Gkanatsios et al. |
| 2016/0034110 A1 | 2/2016 | Edwards |
| 2016/0335395 A1 | 11/2016 | Wu et al. |
| 2017/0038951 A1 | 2/2017 | Reicher |
| 2017/0039321 A1 | 2/2017 | Reicher |
| 2017/0039322 A1 | 2/2017 | Reicher |
| 2017/0039350 A1 | 2/2017 | Reicher |
| 2017/0039705 A1 | 2/2017 | Fram |
| 2017/0046014 A1 | 2/2017 | Fram |
| 2017/0046483 A1 | 2/2017 | Reicher |
| 2017/0046485 A1 | 2/2017 | Reicher |
| 2017/0046495 A1 | 2/2017 | Fram |
| 2017/0046870 A1 | 2/2017 | Fram |
| 2017/0053404 A1 | 2/2017 | Reicher |
| 2017/0200064 A1 | 7/2017 | Reicher |
| 2017/0200269 A1 | 7/2017 | Reicher |
| 2017/0206324 A1 | 7/2017 | Reicher |

(56) References Cited

U.S. PATENT DOCUMENTS

2017/0293720 A1 10/2017 Reicher
2017/0301090 A1 10/2017 Fram
2017/0308647 A1 10/2017 Reicher

OTHER PUBLICATIONS

US 8,208,705, 06/2012, Reicher et al. (withdrawn)
U.S. Appl. No. 14/540,830, Systems and Methods for Viewing Medical Images, filed Nov. 13, 2014,
U.S. Appl. No. 15/254,627, Systems and Methods for Interleaving Series of Medical Images, filed Sep. 1, 2016.
U.S. Appl. No. 14/095,123, Systems and Methods for Retrieval of Medical Data, filed Dec. 3, 2013.
U.S. Appl. No. 15/292,006, Systems and Methods for Viewing Medical 3D Imaging Volumes, filed Oct. 12, 2016.
U.S. Appl. No. 15/346,530, Systems and Methods for Matching, Naming, and Displaying Medical Images, filed Nov. 8, 2016.
U.S. Appl. No. 14/298,806, Smart Placement Rules, filed Jun. 6, 2014.
U.S. Appl. No. 11/942,687, Smart Forms, filed Nov. 19, 2007
U.S. Appl. No. 14/043,165, Automated Document Filings, filed Oct. 1, 2013.
U.S. Appl. No. 11/944,000, Exam Scheduling With Customer Configured Notifications, filed Nov. 21, 2007.
U.S. Appl. No. 15/292,014, System and Method of Providing Dynamic and Customizable Medical Examination for, filed Oct. 12, 2016.
U.S. Appl. No. 15/292,023, Selective Display of Medical Images, filed Oct. 12, 2016.
U.S. Appl. No. 14/792,210, Dynamic Montage Reconstruction, filed Jul. 6, 2015.
U.S. Appl. No. 15/188,872, Intelligent Management of Computerized Advanced Processing, filed Jun. 21, 2016.
U.S. Appl. No. 15/188,819, Intelligent Management of Computerized Advanced Processing, filed Jun. 21, 2016.
U.S. Appl. No. 15/140,346, Database Systems and Interactive User Interfaces for Dynamic Interaction With, and Sorting of, Digital Medical Image Data, filed Apr. 27, 2106.
U.S. Appl. No. 15/140,363, Database Systems and Interactive User Interfaces for Dynamic Interation With, and Comparison of, Digital Medical Image Data, filed Apr. 27, 2016.
U.S. Appl. No. 15/140,351, Database Systems and Interactive User Interfaces for Dynamic Interaction With, and Review of, Digital Medical Image Data, filed Apr. 27, 2016.
U.S. Appl. No. 15/140,348, Database Systems and Interactive User Interfaces for Dynamic Interaction With, and Indications of, Digital Medical Image Data, filed Apr. 27, 2016.
AGFA HealthCare, color brochure "IMPAX 6: Digital Image and Information Management," © 2012 Agfa HealthCare N.V. Downloaded from http://www.agfahealthcare.com/global/en/he/library/libraryopen?ID=32882925. Accessed on Feb. 9, 2015.
AGFA HealthCare, IMPAX 6.5 Datasheet (US)2012. © 2012 Agfa HealthCare N.V. Downloaded from http://www.agfahealthcare.com/global/en/he/library/libraryopen?ID=37459801. Accessed on Feb. 9, 2015.
AMD Technologies, Inc., Catella PACS 5.0 Viewer User Manual (112 pgs), © 2010, AMD Technologies, Inc. (Doc. 340-3-503 Rev. 01). Downloaded from http://www.amdtechnologies.com/lit/cat5viewer.pdf. Accessed on Feb. 9, 2015.
ASPYRA's Imaging Solutions, 3 page color print out. Accessed at http://www.aspyra.com/imaging-solutions. Accessed on Feb. 9, 2015.
AVREO, interWorks—RIS/PACS package, 2 page color brochure, © 2014, Avreo, Inc. (Document MR-5032 Rev. 4). Downloaded from http://www.avreo.com/ProductBrochures/MR-5032Rev.%204interWORKS%20RISPACSPackage.pdf. Accessed on Feb. 9, 2015.
BRIT Systems, BRIT PACS View Viewer, 2 page color brochure, (BPB-BPV-0001). Downloaded from http://www.britcom/pdfs/britpacsview.pdf. Accessed on Feb. 9, 2015.
BRIT Systems, Roentgen Works—100% Browers-based VNA (Vendor Neutral Archive/PACS), © 2010 BRIT Systems, 1 page color sheet. Accessed at http://www.roentgenworks.com/PACS. Accessed on Feb. 9, 2015.
BRIT Systems, Vision Multi-modality Viewer—with 3D, 2 page color brochure, (BPB-BVV-0001 REVC). Downloaded from http://www.brit.com/pdfs/BPB-BVV-0001REVC_BRIT_Vision_Viewer.pdf. Accessed on Feb. 9, 2015.
CANDELiS, ImageGrid™: Image Management Appliance, 6 page color brochure. (AD-012 Rev. F Nov. 2012), © 2012 Candelis, Inc. Downloaded from http://www.candelis.com/images/pdf/Candelis_ImageGrid_Appliance_20111121.pdf. Accessed on Feb. 9, 2015.
Carestream, Cardiology PACS, 8 page color brochure. (CAT 866 6075 06/12). © Carestream Health, Inc., 2012. Downloaded from http://www.carestream.com/cardioPACS_brochure_M1-877.pdf. Accessed on Feb. 9, 2015.
Carestream, Vue PACS, 8 page color brochure. (CAT 300 1035 05/14). © Carestream Health, Inc., 2014. Downloaded from http://www.carestream.com/csPACS_brochure_M1-876.pdf. Accessed on Feb. 9, 2015.
Cerner, Radiology—Streamline image management, 2 page color brochure, (fl03_332_10_v3). Downloaded from http://www.cerner.com/uploadedFiles/Clinical_Imaging.pdf. Accessed on Feb. 9, 2015.
CoActiv, EXAM-PACS, 2 page color brochure, © 2014 CoActiv, LLC. Downloaded from http://coactiv.com/wp-content/uploads/2013/08/EXAM-PACS-BROCHURE-final-web.pdf. Accessed on Feb. 9, 2015.
Crowley, Rebecca et al., Development of Visual Diagnostic Expertise in Pathology: an Information-processing Study, Jan. 2003, Journal of the American medical Informatics Association, vol. 10, No. 1, pp. 39-51.
DR Systems, Dominator™ Guide for Reading Physicians, Release 8.2, 546 pages, (TCP-000260-A), © 1997-2009, DR Systems, Inc. Downloaded from https://resources.dominator.com/assets/004/6999.pdf. Document accessed Feb. 9, 2015.
DR Systems, DR Scheduler User Guide, Release 8.2, 410 pages, (TCP-000115-A), © 1997-2009, DR Systems, Inc. Downloaded from https://resources.dominator.com/assets/003/6850.pdf. Document accessed Feb. 9, 2015.
Erickson, et al.: "Effect of Automated Image Registration on Radiologist Interpretation," Journal of Digital Imaging, vol. 20, No. 2 Jun. 2007; pp. 105-113.
Erickson, et al.: "Image Registration Improves Confidence and Accuracy of Image Interpretation," Special Issue-Imaging Informatics, Cancer Informatics 2007: 1 19-24.
Fujifilm Medical Systems, SYNAPSE® Product Data, Synapse Release Version 3.2.1, Foundation Technologies, 4 page color brochure, (XBUSSY084) Aug. 2008. Downloaded from http://www.fujifilmusa.com/shared/bin/foundation.pdf. Accessed on Feb. 9, 2015.
Fujifilm Medical Systems, SYNAPSE® Product Data, Synapse Release Version 3.2.1, Server Modules and Interfaces, 4 page color brochure, (XBUSSY085) Aug. 2008. Downloaded from http://www.fujifilmusa.com/shared/bin/server-interface.pdf. Accessed on Feb. 9, 2015.
Fujifilm Medical Systems, SYNAPSE® Product Data, Synapse Release Version 3.2.1, Workstation Software, 4 page. color brochure, (XBUSSY082) Aug. 2008. Downloaded from http://www.fujifilmusa.com/shared/bin/workstation.pdf. Accessed on Feb. 9, 2015.
GE Healthcare, Centricity PACS, in 8 page printout. Accessed at http://www3.gehealthcare.com/en/products/categories/healthcare_it/medical_imaging_informatics_-_ris-pacs-cvis/centricity_pacs. Accessed on Feb. 9, 2015.
Handylife.com—Overview of Handy Patients Enterprise, in 2 page printout. Accessed from http://www.handylife.com/en/software/overview.html. Accessed on Feb. 18, 2015.
Handylife.com—Features of Handy Patients Enterprise, in 4 page printout. Accessed from http://www.handylife.com/en/software/features.html. Accessed on Feb. 18, 2015.

(56) References Cited

OTHER PUBLICATIONS

Handylife.com—Screenshots of Handy Patients Enterprise, in 2 page printout. Accessed from http://www.handylife.com/en/software/screenshots.html. Accessed on Feb. 18, 2015.
iCRco, I See the Future, in 12 pages, color brochure, (BR080809AUS), © 2009 iCRco.ClarityPACS. Downloaded from http://www.claritypacs.com/pdfs/ISeeFuture_26_Web.pdf. Accessed on Feb. 9, 2015.
Imageanalysis, dynamika, 2 page color brochure. Downloaded from http://www.imageanalysis.org.uk/what-we-do. Accessed on Feb. 9, 2015.
Imageanalysis, MRI Software, in 5 page printout. Accessed at http://www.imageanalysis.org.uk/mri-software. Accessed on Feb. 9, 2015.
IMSI, Integrated Modular Systems, Inc., Hosted / Cloud PACS in one page printout. Accessed at http://www.imsimed.com/#!products-services/ctnu. Accessed on Feb. 9, 2015.
Infinitt, PACS, RIS, Mammo PACS, Cardiology Suite and 3D/Advanced Visualization | Infinittna, 2 page printout. Accessed at http://www.infinittna.com/products/radiology/radiology-pacs. Accessed on Feb. 9, 2015.
Intelerad, IntelePACS, 2 page color brochure, © 2014 Intelerad Medical Systems Incoprorated. Downloaded http://www.intelerad.com/wp-content/uploads/sites/2/2014/08/IntelePACS-brochure.pdf. Accessed on Feb. 9, 2015.
Intelerad, InteleViewer, 2 page color brochure, © 2014 Intelerad Medical Systems Incoprorated. Downloaded from http://www.intelerad.com/wp-content/uploads/sites/2/2014/09/InteleViewer-brochure.pdf. Accessed on Feb. 9, 2015.
Intuitive Imaging Informatics, ImageQube, 1 page in color. Downloaded from http://www.intuitiveimaging.com/2013/pdf/ImageQube%20one-sheet.pdf. Accessed on Feb. 9, 2015.
Kuhl, Helen: Comparison Chart/PACS, Customers Are Happy, But Looking for More, (color) Imaging Techology News, itnonline.com, May 2012, pp. 24-27. Downloaded from http://www.merge.com/MergeHealthcare/media/company/In%20The%20News/merge-pacs-comparison.pdf. Accessed on Feb. 9, 2015.
LUMEDX CardioPACS 5.0 Web Viewer, Cardiopacs Module, 2 page color brochure, (506-10011 Rev A). Downloaded from http://cdn.medicexchange.com/images/whitepaper/cardiopacs_web_viewer.pdf?1295436926. Accessed on Feb. 9, 2015.
LUMEDX Cardiovascular Information System, CardioPACS, one page In color printout. Accessed at http://www.lumedx..com/pacs.aspx. Accessed on Feb. 9, 2015.
McKesson Enterprise Medical Imagining and PACS | McKesson, 1 page (color) printout. Accessed at http://www.mckesson.com/providers/health-systems/diagnostic-imaging/enterprise-medical-imaging. Accessed on Feb. 9, 2015.
Medweb Radiology Workflow Solutions, Radiology Workflow Solutions, Complete Workflow & Flexible Turnkey Solutions, Web RIS/PACS with Advanced Viewer, 3 page color brochure, © 2006-2014 Medweb. Downloaded from http://www.medweb.com/docs/rispacs_brochure_2014.pdf. Accessed on Feb. 9, 2015.
Mendelson, et al., "Informatics in Radiology—Image Exchange: IHE and the Evolution of Image Sharing," RadioGraphics, Nov.-Dec. 2008, vol. 28, No. 7.
Merge Radiology Solutions, Merge PACS, A real-time picture archiving communication system, (PAX-21990 rev 2.0), 2 page color brochure. Downloaded from http://www.merge.com/MergeHealthcare/media/documents/brochures/Merge_PACS_web.pdf. Accessed on Feb. 9, 2015.
NOVARAD Enterprise Imaging Solutions, NOVAPACS, 2 page (color) printout. Accessed at http://ww1.novarad.net/novapacs. Accessed on Feb. 9, 2015.
PACSPLUS, PACSPLUS Server, 1 page (color) printout. Accessed at http://www.pacsplus.com/01_products/products_01.html. Accessed on Feb. 9, 2015.
PACSPLUS, PACSPLUS Workstation, 3 page (color) printout. Accessed at http://www.pacsplus.com/01_products/products_01.html. Accessed on Feb. 9, 2015.
Philips IntelliSpace PACS, in 2 color page printout. Accessed at https://www.healthcare.philips.com/main/products/healthcare_informatics/products/enterprise_imaging _informatics/isite_pacs. Accessed on Feb. 9, 2015.
Philips, IntelliSpace: Multi-modality tumor tracking application versus manual PACS methods, A time study for Response Evaluation Criteria in Solid Tumors (RECIST). 2012, Koninklijke Philips Electronics N.V., in four pages.
RamSoft, RIS PACS Teleradiology, PowerServer PACS, Lite PACS, XU PACS Compare RamSoft PACS Products, 2 color page printout. Accessed at http://www.ramsoft.com/products/powerserver-pacs-overview. Accessed on Feb. 9, 2015.
Rosset et al.: "OsiriX:Aan Open-Source Software for Navigating in Multidimensional DICOM Images," Journal of digital Imaging, Sep. 2004, pp. 205-216.
Sage Intergy PACS | Product Summary. Enhancing Your Workflow by Delivering Web-based Diagnostic Images When and Where You Need Them, in 2 color pages (IRV-SS-INTPACS-PSS-031309). © 2009 Sage Software Healcare, Inc. Downloaded from http://www.greenwayhealth.com/solutions/intergy/. Accessed on Feb. 9, 2015.
Sandberg, et al., "Automatic detection and notification of "wrong paitent-wrong location" errors in the operating room," Surgical Innovation, vol. 12, No. 3, Sep. 2005, pp. 253-260.
Schellingerhout, Dawid, MD, et al.: "Coregistration of Head CT Comparison Studies: Assessment of Clinical Utility," Acad Radiol 2003; 10:242-248.
ScImage, Cardiology PACS, in 8 color page printout. Accessed at http://www.scimage.com/solutions/clinical-solutions/cardiology. Accessed on Feb. 9, 2015.
Sectra RIS PACS, in 2 color page printout. Accessed at https://www.sectra.com/medical/diagnostic_imaging/solutions/ris-pacs/. Accessed on Feb. 9, 2015.
Siemens syngo.plaza, Features and Benefits, in 2 color page printout. Accessed at http://www.healthcare.siemens.com/medical-imaging-it/imaging-it-radiology-image-management-pacs/syngoplaza/features. Accessed on Feb. 9, 2015.
Simms | RIS and PACS Medical Imaging Software, in 2 color page printout. http://www.mysimms.com/ris-pacs.php. Accessed on Feb. 9, 2015.
Sprawls, "Image Characteristics and Quality," Physical Principles of Medical Imaging, http://www.sprawls.org/resources pp. 1-14.
Stryker, Imaging—OfficePACS Power Digital Imaging, in one color page printout. Accessed from http://www.stryker.com/emea/Solutions/Imaging/OfficePACSPowerDigitalImaging/index.htm. Accessed on Feb. 9, 2015.
Stryker, OfficePACS Power—Digital Imaging, 8 page color brochure, (MPP-022 Rev 4 BC/MP 300 1/07). © 2007 Stryker. Downloaded from http://www.stryker.com/emea/Solutions/Imaging/OfficePACSPowerDigitalImaging/ssLINk/emea/1557/022268. Accessed on Feb. 9, 2015.
TeraRecon iNtuition pamphlet in 20 pages, retrieved on Nov. 8, 2013, available at http://int.terarecon.com/wp-content/uploads/2013/11/brochure_english2013.pdf.
TeraRecon iNtuition—Workflow. <www.terarecon.com/wordpress/our-solutions/intuition-workflow> Last accessed Nov. 8, 2013. 2 pages.
UltraRAD—ultra VISION, 1 page (color). Downloaded from http://www.ultraradcorp.com/pdf/UltraVISION.pdf. Accessed on Feb. 9, 2015.
VioStream for VitreaView, 2 color pages printout. Accessed at http://www.vitalimages.com/solutions/universal-viewing/viostream-for-vitreaview. Accessed on Feb. 9, 2015.
Visage Imaging Visage 7, 3 color page printout. Accessed at http://www.visageimaging.com/visage-7. Accessed on Feb. 9, 2015.
VIZTEK Radiology PACS Software Vixtek Opal-RAD, 4 color page printout. Accessed at http://viztek.net/products/opal-rad. Accessed on Feb. 9, 2015.

(56) References Cited

OTHER PUBLICATIONS

Voyager Imaging—Voyager PACS Radiologist Workstation, 2 page color brochure. Downloaded from http://www.intellirad.com.au/assets/Uploads/Voyager-PacsWorkstations.pdf?. Accessed on Feb. 9, 2015.
Voyager Imaging—Voyager PACS, 3 page color brochure. Downloaded from http://www.intellirad.com.au/index.php/assets/Uploads/Voyager-Pacs3.pdf. Accessed on Feb. 9, 2015.
Ivetic, D., and Dragan, D., Medical Image on the Go!, 2009, J Med Syst, vol. 35, pp. 499-516.
Tahmoush,D. and Samet, H., A New Database for Medical Images and Information, 2007, Medical Imaging 2007; PACS and Imaging Informatics, vol. 6516. pp. 1-9.
Non-Final Office Action dated Aug. 28, 2007 in U.S. Appl. No. 11/179,384.
Final Office Action dated Jun. 26, 2008 in U.S. Appl. No. 11/179,384.
Non-Final Office Action dated Dec. 29, 2008 in U.S. Appl. No. 11/179,384.
Final Office Action dated Jul. 24, 2009, in U.S. Appl. No. 11/179,384.
Notice of Allowance dated Nov. 3, 2009, in U.S. Appl. No. 11/179,384.
Non-Final Office Action dated Aug. 18, 2010 in U.S. Appl. No. 12/702,976.
Interview Summary dated Dec. 1, 2010, in U.S. Appl. No. 12/702,976.
Final Office Action dated Feb. 17, 2011 in U.S. Appl. No. 12/702,976.
Interview Summary dated May 31, 2011 in U.S. Appl. No. 12/702,976.
Notice of Allowance dated Jul. 20, 2011, in U.S. Appl. No. 12/702,976.
Office Action dated Dec. 1, 2011, in U.S. Appl. No. 13/228,349.
Notice of Allowance dated Feb. 6, 2012, in U.S. Appl. No. 13/228,349.
Notice of Allowance dated Jul. 20, 2012, in U.S. Appl. No. 13/228,349.
Office Action dated Dec. 11, 2013, in U.S. Appl. No. 13/477,853.
Interview Summary dated Mar. 14, 2014, in U.S. Appl. No. 13/477,853.
Final Office Action dated Jun. 13, 2014, in U.S. Appl. No. 13/477,853.
Notice of Allowance dated Aug. 15, 2014, in U.S. Appl. No. 13/477,853.
Office Action dated Jan. 17, 2017, in U.S. Appl. No. 14/540,830.
Non-Final Office Action dated Oct. 1, 2009, in U.S. Appl. No. 11/268,261.
Notice of Allowance dated Feb. 2, 2010, in U.S. Appl. No. 11/268,261.
Interview Summary dated Jan. 25, 2010, in U.S. Appl. No. 11/268,261.
Interview Summary dated May 14, 2010, in U.S. Appl. No. 11/268,261.
Notice of Allowance dated May 17, 2010, in U.S. Appl. No. 11/268,261.
Supplemental Notice of Allowance dated Aug. 6, 2010, in U.S. Appl. No. 11/268,261.
Issue Notice dated Sep. 1, 2010, in U.S. Appl. No. 11/268,261.
Notice of Allowance dated Oct. 8, 2010, in U.S. Appl. No. 11/268,261.
Notice of Allowance dated Dec. 3, 2010, in U.S. Appl. No. 11/268,261.
Notice of Allowance dated Jan. 6, 2011, in U.S. Appl. No. 11/268,261.
Office Action dated May 16, 2011, in U.S. Appl. No. 12/857,915.
Interview Summary dated Sep. 6, 2011, in U.S. Appl. No. 12/857,915.
Final Office Action dated Dec. 15, 2011, in U.S. Appl. No. 12/857,915.
Office Action dated Jun. 12, 2012, in U.S. Appl. No. 12/857,915.
Office Action dated Aug. 23, 2013, in U.S. Appl. No. 12/857,915.
Interview Summary dated Feb. 4, 2014, in U.S. Appl. No. 12/857,915.
Notice of Allowance dated Jul. 3, 2014, in U.S. Appl. No. 12/857,915.
"Corrected" Notice of Allowance dated Aug. 15, 2014, in U.S. Appl. No. 12/857,915.
Non-Final Office Action dated Jan. 20, 2016, in U.S. Appl. No. 14/502,055.
Interview Summary dated Apr. 14, 2016, in U.S. Appl. No. 14/502,055.
Notice of Allowance dated Jun. 2, 2016, in U.S. Appl. No. 14/502,055.
Notice of Corrected Allowability dated Jul. 14, 2016, in U.S. Appl. No. 14/502,055.
Notice of Corrected Allowability dated Sep. 19, 2016, in U.S. Appl. No. 14/502,055.
Office Action dated Dec. 12, 2016, in U.S. Appl. No. 15/254,627.
Non-Final Office Action dated May 13, 2009, in U.S. Appl. No. 11/265,979.
Final Office Action dated Dec. 22, 2009 in U.S. Appl. No. 11/265,979.
Non-Final Office Action dated Jul. 8, 2010 in U.S. Appl. No. 11/265,979.
Interview Summary dated Mar. 4, 2010 in U.S. Appl. No. 11/265,979.
Interview Summary dated Nov. 16, 2010 in U.S. Appl. No. 11/265,979.
Final Office Action dated Dec. 23, 2010 in U.S. Appl. No. 11/265,979.
Interview Summary dated Mar. 17, 2011 in U.S. Appl. No. 11/265,979.
Notice of Allowance dated May 26, 2011 in U.S. Appl. No. 11/265,979.
Office Action dated Jun. 8, 2012 in U.S. Appl. No. 13/171,081.
Interview Summary dated Jul. 31, 2012 in U.S. Appl. No. 13/171,081.
Final Office Action dated Oct. 12, 2012 in U.S. Appl. No. 13/171,081.
Interview Summary dated Nov. 6, 2012 in U.S. Appl. No. 13/171,081.
Notice of Allowance, dated Sep. 4, 2013, in U.S. Appl. No. 13/171,081.
Office Action dated Mar. 3, 2015 in U.S. Appl. No. 14/095,123.
Interview Summary dated May 1, 2015 in U.S. Appl. No. 14/095,123.
Final Office Action dated Jul. 23, 2015 in U.S. Appl. No. 14/095,123.
Interview Summary dated Aug. 27, 2015 in U.S. Appl. No. 14/095,123.
Office Action dated Feb. 23, 2016 in U.S. Appl. No. 14/095,123.
Final Office Action dated Jul. 20, 2016 in U.S. Appl. No. 14/095,123.
Non-Final Office Action dated Aug. 24, 2009 in U.S. Appl. No. 11/268,262.
Non-Final Office Action dated Apr. 16, 2010 in U.S. Appl. No. 11/268,262.
Interview Summary dated Nov. 24, 2009 in U.S. Appl. No. 11/268,262.
Interview Summary dated May 12, 2010 in U.S. Appl. No. 11/268,262.
Final Office Action dated Oct. 28, 2010 in U.S. Appl. No. 11/268,262.
Interview Summary dated Dec. 1, 2010 in U.S. Appl. No. 11/268,262.
Notice of Allowance dated Dec. 1, 2010 in U.S. Appl. No. 11/268,262.
Notice of Allowance dated Feb. 25, 2011 in U.S. Appl. No. 11/268,262.
Non-Final Office Action dated Jan. 11, 2012 in U.S. Appl. No. 13/079,597.

(56) References Cited

OTHER PUBLICATIONS

Notice of Allowance dated Apr. 25, 2012, in U.S. Appl. No. 13/079,597.
Non-Final Office Action dated Apr. 4, 2013 in U.S. Appl. No. 13/535,758.
Notice of Allowance, dated Aug. 23, 2013 in U.S. Appl. No. 13/535,758.
Corrected Notice of Allowance dated Jun. 27, 2016, in U.S. Appl. No. 14/502,055.
Office Action dated Mar. 10, 2016 in U.S. Appl. No. 14/081,225.
Notice of Allowance dated Sep. 2, 2016 in U.S. Appl. No. 14/081,225.
Corrected Notice of Allowance dated Oct. 21, 2016 in U.S. Appl. No. 14/081,225.
Non-Final Office Action dated Jul. 27, 2009 in U.S. Appl. No. 11/265,978.
Notice of Allowance dated Nov. 19, 2009 in U.S. Appl. No. 11/265,978.
Notice of Allowance dated Apr. 19, 2010 in U.S. Appl. No. 11/265,978.
Supplemental Notice of Allowance dated May 3, 2010 in U.S. Appl. No. 11/265,978.
Supplemental Notice of Allowance dated Aug. 3, 2010 in U.S. Appl.No. 11/265,978.
Non-Final Office Action dated May 5, 2011 in U.S. Appl. No. 12/870,645.
Non-Final Office Action dated May 31, 2013, in U.S. Appl. No. 13/345,606.
Interview Summary dated Aug. 15, 2013, in U.S. Appl. No. 13/345,606.
Notice of Allowance, dated Jan. 9, 2014 in U.S. Appl. No. 13/345,606.
Non-Final Office Action dated Mar. 18, 2016 in U.S. Appl. No. 14/244,431.
Interview Summary dated Jun. 17, 2016 in U.S. Appl. No. 14/244,431.
Notice of Allowance dated Aug. 18, 2016 in U.S. Appl. No. 14/244,431.
Corrected Notice of Allowance dated Nov. 16, 2016 in U.S. Appl. No. 14/244,431.
Non-Final Office Action dated May 26, 2010 in U.S. Appl. No. 11/942,674.
Interview Summary dated Jul. 26, 2010 in U.S. Appl. No. 11/942,674.
Final Office Action dated Nov. 26, 2010 in U.S. Appl. No. 11/942,674.
Interview Summary dated Mar. 2, 2011 in U.S. Appl. No. 11/942,674.
Notice of Allowance, dated Apr. 1, 2011 in U.S. Appl. No. 11/942,674.
Non Final Office Action Dated Nov. 10, 2011 in U.S. Appl. No. 13/118,085.
Interview Summary, dated Feb. 17, 2012, in U.S. Appl. No. 13/118,085.
Final Office Action, dated Apr. 13, 2012, in U.S. Appl. No. 13/118,085.
Notice of Allowance, dated Feb. 6, 2013, in U.S. Appl. No. 13/118,085.
Non Final Office Action dated Aug. 23, 2013 in U.S. Appl. No. 13/907,128.
Final Office Action dated Oct. 9, 2013 in U.S. Appl. No. 13/907,128.
Interview Summary dated Nov. 22, 2013 in U.S. Appl. No. 13/907,128.
Notice of Allowance dated Jan. 31, 2014 in U.S. Appl. No. 13/907,128.
Office Action, dated Dec. 29, 2014 in U.S. Appl. No. 14/298,806.
Interview Summary, dated Mar. 2, 2015 in U.S. Appl. No. 14/298,806.
Final Office Action, dated Jun. 17, 2015 in U.S. Appl. No. 14/298,806.
Office Action, dated Feb. 16, 2016 in U.S. Appl. No. 14/298,806.
Final Office Action, dated Jul. 21, 2016 in U.S. Appl. No. 14/298,806.
Non Final Office Action dated Sep. 16, 2010 in U.S. Appl. No. 11/942,687.
Interview Summary dated Dec. 3, 2010 in U.S. Appl. No. 11/942,687.
Final Office Action, dated Apr. 5, 2011 in U.S. Appl. No. 11/942,687.
Office Action, dated Mar. 13, 2014 in U.S. Appl. No. 11/942,687.
Interview Summary, dated Jun. 17, 2014 in U.S. Appl. No. 11/942,687.
Office Action, dated Jul. 18, 2014 in U.S. Appl. No. 11/942,687.
Final Office Action, dated Jan. 5, 2015 in U.S. Appl. No. 11/942,687.
Interview Summary, dated Mar. 4, 2015 in U.S. Appl. No. 11/942,687.
PTAB Examiner's Answer, dated Feb. 25, 2016 in U.S. Appl. No. 11/942,687.
Non-Final Office Action dated Apr. 14, 2010 in U.S. Appl. No. 11/944,027.
Interview Summary dated May 13, 2010 in U.S. Appl. No. 11/944,027.
Final Office Action dated Dec. 23, 2010 in U.S. Appl. No. 11/944,027.
Interview Summary dated Mar. 31, 2011 in U.S. Appl. No. 11/944,027.
Office Action dated Apr. 19, 2012 in U.S. Appl. No. 11/944,027.
Interview Summary dated Jun. 28, 2012 in U.S. Appl. No. 11/944,027.
Final Office Action dated Oct. 22, 2012 in U.S. Appl. No. 11/944,027.
Notice of Allowance dated Jun. 5, 2013 in U.S. Appl. No. 11/944,027.
Office Action dated Oct. 14, 2014 in U.S. Appl. No. 14/043,165.
Final Office Action dated Apr. 1, 2015 in U.S. Appl. No. 14/043,165.
Office Action dated Oct. 2, 2015 in U.S. Appl. No. 14/043,165.
Interview Summary dated Dec. 21, 2015 in U.S. Appl. No. 14/043,165.
Final Office Action dated Feb. 17, 2016 in U.S. Appl. No. 14/043,165.
Appeal Brief dated Jul. 15, 2016 in U.S. Appl. No. 14/043,165.
Examiner's Answer dated Nov. 14, 2016, in U.S. Appl. No. 14/043,165.
Non-Final Office Action dated Sep. 29, 2010 in U.S. Appl. No. 11/944,000.
Final Office Action dated Apr. 20, 2011 in U.S. Appl. No. 11/944,000.
Interview Summary dated Jun. 7, 2011 in U.S. Appl. No. 11/944,000.
Appeal Brief dated Mar. 4, 2013 in U.S. Appl. No. 11/944,000.
Examiner's Answer dated Jun. 26, 2013 in U.S. Appl. No. 11/944,000.
Board Decision dated Mar. 23, 2016 in U.S. Appl. No. 11/944,000.
Office Action, dated Jul. 15, 2016 in U.S. Appl. No. 11/944,000.
Notice of Allowance, dated Jan. 30, 2017, in U.S. Appl. No. 11/944,000.
Office Action dated Feb. 3, 2012 in U.S. Appl. No. 12/622,404.
Interview Summary dated May 8, 2012 in U.S. Appl. No. 12/622,404.
Final Office Action dated Aug. 6, 2012 in U.S. Appl. No. 12/622,404.
Notice of Allowance dated Oct. 15, 2012 in U.S. Appl. No. 12/622,404.
Office Action dated Mar. 17, 2015 in U.S. Appl. No. 13/768,765.
Interview Summary dated Jun. 11, 2015 in U.S. Appl. No. 13/768,765.
Notice of Allowance dated Aug. 28, 2015 in U.S. Appl. No. 13/768,765.
Notice of Allowability dated Nov. 20, 2015 in U.S. Appl. No. 13/768,765.
Notice of Allowability dated Jul. 28, 2016 in U.S. Appl. No. 13/768,765.

(56) References Cited

OTHER PUBLICATIONS

Office Action dated Mar. 4, 2013 in U.S. Appl. No. 12/891,543.
Interview Summary dated Apr. 5, 2013 in U.S. Appl. No. 12/891,543.
Notice of Allowance dated Nov. 14, 2013 in U.S. Appl. No. 12/891,543.
Office Action dated Sep. 11, 2014 in U.S. Appl. No. 14/179,328.
Notice of Allowance dated Jan. 14, 2015 in U.S. Appl. No. 14/179,328.
Office Action dated Aug. 13, 2015 in U.S. Appl. No. 14/687,853.
Notice of Allowance dated Feb. 25, 2016 in U.S. Appl. No. 14/687,853.
Supplemental Notice of Allowance dated Jun. 2, 2016 in U.S. Appl. No. 14/687,853.
Notice of Allowance dated Aug. 11, 2016 in U.S. Appl. No. 15/163,600.
Supplemental Notice of Allowance dated Sep. 14, 2016 in U.S. Appl. No. 15/163,600.
Office Action dated Jun. 27, 2014 in U.S. Appl. No. 13/572,397.
Final Office Action dated Jan. 13, 2015 in U.S. Appl. No. 13/572,397.
Notice of Allowance dated Mar. 19, 2015, 2015 in U.S. Appl. No. 13/572,397.
Office Action dated Aug. 6, 2014 in U.S. Appl. No. 13/572,547.
Notice of Allowance, dated Mar. 3, 2015 in U.S. Appl. No. 13/572,547.
Corrected Notice of Allowance, dated Apr. 10, 2015 in U.S. Appl. No. 13/572,547.
Corrected Notice of Allowance, dated May 21, 2015 in U.S. Appl. No. 13/572,547.
Office Action dated Jul. 30, 2014 in U.S. Appl. No. 13/572,552.
Interview Summary dated Sep. 3, 2014 in U.S. Appl. No. 13/572,552.
Final Office Action dated Jan. 28, 2015 in U.S. Appl. No. 13/572,552.
Interview Summary dated Apr. 23, 2015 in U.S. Appl. No. 13/572,552.
Notice of Allowance, dated May 8, 2015 in U.S. Appl. No. 13/572,552.
Restriction Requirement, dated Jul. 28, 2015 in U.S. Appl. No. 14/139,068.
Office Action, dated Mar. 11, 2016 in U.S. Appl. No. 14/139,068.
Notice of Allowance, dated Sep. 21, 2016 in U.S. Appl. No. 14/139,068.
Office Action, dated Jan. 12, 2017 in U.S. Appl. No. 15/292,023.
U.S. Appl. No. 15/631,313, Systems and Methods for Interleaving Series of Medical Images, filed Jun. 23, 2017.
U.S. Appl. No. 15/631,291, Systems and Methods for Retrieval of Medical Data, filed Jun. 23, 2017.
U.S. Appl. No. 15/646,756, Smart Placement Rules, filed Jul. 11, 2017.
U.S. Appl. No. 15/475,930, Exam Scheduling With Customer Configured Notifications, filed Mar. 31, 2017.
U.S. Appl. No. 15/469,342 Rules-Based Rendering of Medical Images, filed Mar. 24, 2017.
U.S. Appl. No. 15/469,281, Rules-Based Processing and Presentation of Medical Images, filed Mar. 24, 2017.
Interview Summary dated Mar. 24, 2017, in U.S. Appl. No. 14/540,830.
Final Office Action dated May 15, 2017, in U.S. Appl. No. 14/540,830.
Interview Summary dated Jul. 28, 2017, in U.S. Appl. No. 14/540,830.
Notice of Allowance dated Aug. 15, 2017, in U.S. Appl. No. 14/540,830.
Notice of Allowance dated Apr. 3, 2017 in U.S. Appl. No. 15/254,627.
Notice of Allowance (corrected) dated Jul. 13, 2017 in U.S. Appl. No. 15/254,627.
Notice of Allowance dated Mar. 30, 2017 in U.S. Appl. No. 14/095,123.
Notice of Allowance, dated Apr. 12, 2017 in U.S. Appl. No. 14/298,806.
Notice of Allowance, dated Apr. 11, 2017 in U.S. Appl. No. 15/292,023.
Office Action dated Jun. 27, 2017 in U.S. Appl. No. 15/469,342.
Office Action dated Jun. 26, 2017 in U.S. Appl. No. 15/469,281.
U.S. Appl. No. 15/799,657, filed Oct. 31, 2017 including its ongoing prosecution history, including without limitation Office Actions, Amendments, Remarks, and any other potentially relevant documents, Reicher et al.
Examiner's Decision on Appeal dated Dec. 22, 2017 in U.S. Appl. No. 11/942,687.
Examiner's Decision on Appeal dated Dec. 20, 2017, in U.S. Appl. No. 14/043,165.
Office Action, dated Jan. 10, 2018 in U.S. Appl. No. 15/475,930.
Notice of Allowance dated Nov. 30, 2017 in U.S. Appl. No. 15/469,342.
Final Office Action dated Jan. 11, 2018 in U.S. Appl. No. 15/469,281.
Interview Summary dated Oct. 13, 2017 in U.S. Appl. No. 15/469,342.
Interview Summary dated Oct. 13, 2017 in U.S. Appl. No. 15/469,281.

\* cited by examiner

Sample Categories of Properties/Attributes on Which Transfer or Display Rules May be Based

|  |
| --- |
| Slice Thickness |
| # of Images in Series |
| Client Properties (e.g., Client ID) |
| Connection (e.g., Minimum Bandwidth) |
| Site Properties (e.g., Site ID) |
| User Properties (e.g., User ID and/or Role) |
| Exam Properties (e.g., Exam Type) |
| Temporal (e.g., Day, Time, Etc.) |
| Exam Attributes |
| Series Attributes |
| Image Attributes (e.g., Image Plane) |
| Prior Exam Display Attributes |

FIG. 2

User-Defined Rules

| User Info | |
|---|---|
| User ID | JSMITH1221 |
| User Type | Radiologist |
| | |
| Thin Slice Definition | |
| Slice Thickness: | <1mm or |
| # of Images in Series | >400 |
| | |
| Device | Home |
| Download | Upon Request |
| Include on Physical Media | No |
| Include in Print | No |
| Include in Upload | Ask |
| Display as Part of Series | No |
| Delete After | 2 Months |
| Compression Type | Smallest file size |
| Display Preference 1 | FOV 1 |
| Display Preference 2 | W/L 1 |
| Display Preference 3 | 0.5mm Thick |
| Display Preference 4 | 0.2mm Increment |
| Render Location | Server |
| Keep Re-rendered Images | Yes |
| | |
| -Exceptions | |
| Image Type | CT |
| Download | All |
| Include on Physical Media | No |
| Include in Print | Yes |
| Include in Upload | Ask |
| Display as Part of Series | Only in Volume Rendering Mode |
| Delete After | 2 Months |
| Compression Type | Smallest File Size |
| Display Preferences | FOV 2; 0.7mm Thick |

| Device | Hospital |
|---|---|
| Download | All |
| Include on Physical Media | No |
| Include in Print | No |
| Include in Upload | Yes |
| Display as Part of Series | Yes |
| Delete After | Never |
| Compression Type | Lowest Loss |
| Display Preferences | Default to User | ~326
| Render Location | Server | ~328

FIG. 3B

Site Rules

| Site Info | | |
|---|---|---|
| Site ID | Hospital-A | |
| Site Type | Hospital | |
| | | |
| Thin Slice Definition | | User Override Allowed? |
| Slice Thickness: | <2mm | Yes |
| # of Images in Series | | |
| | | |
| Default Rules | | |
| Upload | All | Yes |
| Include on Physical Media | Yes | Yes |
| Include in Print | No | Yes |
| Display as Part of Series | Yes | Yes |
| Delete After | Never | No |
| Compression Type | Lowest Loss | Yes |
| Display Preferences | Default | Yes |

Additional Example Display Rules

| | Condition | Action |
|---|---|---|
| 602 | Slice Thickness<0.5mm | Reformat to 3mm Thickness |
| 604 | Tomo & Slice Thickness<0.5mm | Reformat to 2mm Thickness |
| 606 | Patient Age<30Years & Tomo | Reformat to 0.5mm Thickness & Overlap 0.1mm |
| 608 | Oblique View | Reformat to 4mm Thickness |
| 610 | Patient High Risk | Reformat to 1mm Thickness |
| 612 | # Slices>1000 | Reformat to 4mm & 1mm Overlap |
| 614 | Tissue Density>5(CAP) | Reformat to 1mm |
| 616 | Abnormality Detected (CAP) | Fuse Subset of Relevant Images |

FIG. 6

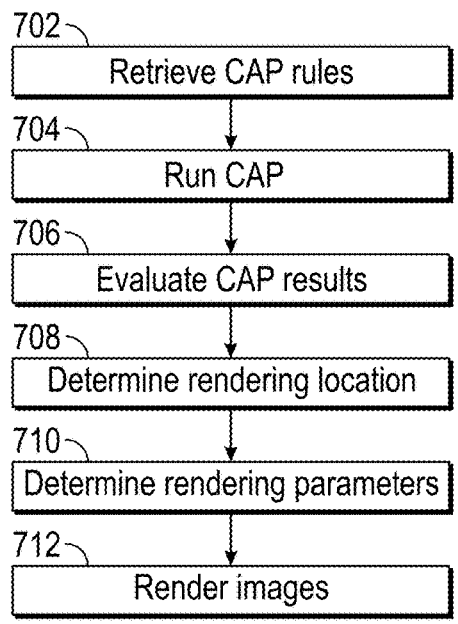

FIG. 7

| Modality | Exam | CAP | Rule to Run Cap |
|---|---|---|---|
| CT | Chest | Spine Fracture Detection | (Clinical Indication is "Trauma" or "Pain" or "History of Fracture") and Approved by Insurance |
| CT | Chest | Lung Nodule Detection | Always |
| CT | Chest | Lung Parenchyma Analysis | On-Demand Per Radiologist |
| CT | Abdomen | Spine Fracture Detection | (Clinical Indication is "Trauma" or "Pain" or "History of Fracture") and Approved by Insurance |
| CT | Abdomen | Liver Analysis (Mass/Volume/Density) | When Ordered by Referring Physician |
| CT | Thoracic Spine | Spine Fracture Detection | Always |
| CT | Lumbar Spine | Spine Fracture Detection | Always |
| CT | Brain Perfusion | CT Brain Perfusion Analysis | Always |
| MRI | Brain With Contrast | MRI Brain Tumor Size | Tumor |
| MRI | Brain With Contrast | MRI Brain Tumor Change Detection | Tumor and Prior Exam |
| MRI | Brain Perfusion | MRI Brain Perfusion Analysis | Always |
| MRI | Brain | MRI Brain Volumetric Analysis | "Dementia" |
| MRI | Brain | MRI Brain CSF Analysis | "Hydrocephalus" or Abnormal Brain Volumetric Analysis |
| MRI | Brain MRA | MRA Brain Aneurysm Detection CAD | Always |
| CT | Brain CTA | 3D Vessel Tracking | On-Demand |
| CT | Brain CTA | Brain Vessel Stenosis CAD | On Demand (Automatically Run 3D Vessel Tracking First) |
| CT | Brain CTA | Brain Aneurysm Detection CAD | On Demand (Automatically Run 3D Vessel Tracking First) |

FIG. 8A

| Computerized Advanced Processing Rules |
|---|
| If ((Imaging Exam is CT of Chest) and (Clinical Indication Includes "Trauma") and (Approved by Insurance)) then Run (Spine Fracture Detection CAD) |
| If (Imaging Exam is CT of Chest) then Run(Lung Nodule Detection CAD) |
| If ((Imaging Exam is CT of Abdomen) and (Clinical Indication Includes "Trauma") and (Approved by Insurance)) then Run (Spine Fracture Detection CAD) |
| If (Imaging Exam is CT of Thoracic Spine) then Run (Spine Fracture Detection CAD) |
| If ((Imaging Exam is MRI of Brain) and (Clinical Indication Includes "Dementa")) then Run (MRI Brain Volumetric Analysis Processing) |
| If ((Imaging Exam is MRI of Brain) and ((Clinical Indication Includes "Hydrocephalus") or (MRI Brain Volume Analysis is Abnormal))) then Run (MRI CSF Analysis Processing) |
| If (Imaging Exam is MRA of Brain) then Run (MRA Brain Aneurysm Detection CAD) |
| If ((Imaging Exam is CTA of Brain) and (Clinical Indication Includes Stroke)) then Run (3D Vessel Tracking) and then Run(Brain Vessel Stenosis CAD) and then Run(Brain Aneurysm Detection CAD) |

FIG. 8B

COMPUTER-AIDED ANALYSIS AND RENDERING OF MEDICAL IMAGES USING USER-DEFINED RULES

CROSS-REFERENCE TO RELATED APPLICATIONS

This application is a continuation-in-part of U.S. patent application Ser. No. 15/292,023 filed on Oct. 12, 2016, titled "Selective Display of Medical Images," which application is a continuation of U.S. patent application Ser. No. 15/163,600 filed on May 24, 2016, titled "Selective Display of Medical Images," which application is a continuation of U.S. patent application Ser. No. 14/687,853 filed on Apr. 15, 2015, titled "Selective Processing of Medical Images," which application is a continuation of U.S. patent application Ser. No. 14/179,328 filed on Feb. 12, 2014, titled "Rules-Based Approach to Rendering Medical Images," which application is a continuation of U.S. patent application Ser. No. 12/891,543 filed on Sep. 27, 2010, titled "Rules-Based Approach to Transferring and/or Viewing Medical Images," which application claims the benefit of priority from U.S. Provisional Patent Application No. 61/246,479 filed on Sep. 28, 2009, titled "Rules-Based Approach to Transferring and/or Viewing Medical Images." The entire disclosure of each of the above items is hereby made part of this specification as if set forth fully herein and incorporated by reference for all purposes, for all that it contains.

This application is also related to U.S. patent application Ser. No. 15/469,342, filed on Mar. 24, 2017, and titled "RULES-BASED RENDERING OF MEDICAL IMAGES," and U.S. patent application Ser. No. 15/469,281, filed on Mar. 24, 2017, and titled "RULES-BASED PROCESSING AND PRESENTATION OF MEDICAL IMAGES." The entire disclosure of each of the above items is hereby made part of this specification as if set forth fully herein and incorporated by reference for all purposes, for all that it contains.

Any and all applications for which a foreign or domestic priority claim is identified in the Application Data Sheet as filed with the present application are hereby incorporated by reference under 37 CFR 1.57 for all purposes and for all that they contain.

All publications and patent applications mentioned in this specification are hereby incorporated by reference in their entirety to the same extent as if each individual publication or patent application was specifically and individually indicated to be incorporated by reference.

TECHNICAL FIELD

This disclosure relates to medical image analysis, medical image processing, medical image rendering, medical image transformation, medical image transferring, and/or medical image viewing.

BACKGROUND

Medical imaging is increasingly moving into the digital realm. This includes imaging techniques that were traditionally analog, such as mammography, x-ray imaging, angiography, endoscopy, and pathology, where information can now be acquired directly using digital sensors, or by digitizing information that was acquired in analog form. Many imaging modalities are inherently digital, such as computed radiography (CR), digital radiography (DR), MRI (magnetic resonance imaging), CT (computed tomography), PET (positron emission tomography), NM (nuclear medicine scanning), FFDM (full-field digital mammography), and US (ultrasound), often yielding hundreds or even thousands of images per examination. Increasingly these digital images are viewed, manipulated, and interpreted using computers and related computer equipment. Accordingly, improved systems and methods are needed for distributing, viewing, and prioritizing these digital images under various network and viewing conditions.

SUMMARY

The systems, methods, and devices described herein each have several aspects, no single one of which is solely responsible for its desirable attributes. Without limiting the scope of this disclosure, several non-limiting features will now be described briefly.

In one embodiment, a method of selecting medical images of an image series for transfer comprises, by a computing device executing software, performing operations comprising, accessing transfer rules associated with a first computing device, the transfer rules indicating thin slice criteria for determining whether respective medical images of an image series are classified as thin slices, wherein the thin slice criteria include at least one of a maximum thickness of a particular medical image for classification of the particular image as a thin slice image or a maximum quantity of medical images in the image series for classification of the medical images of the image series as thin slice images, selecting a first group of medical images of the image series that are thin slice images as indicated by the thin slice criteria, initiating transfer of the first group of medical images to the first computing device, wherein medical images of the image series that are not in the first group are not transferred to the first computing device.

In one embodiment, a method comprises, by a computing device comprising hardware, performing operations comprising accessing thin slice criteria for determining whether respective medical images of an image series are classified as thin slices, selecting a thin slice series of medical images that includes one or more medical images that are classified as thin slices based on the thin slice criteria, selecting a non-thin slice series of medical images that includes one or more medical images that are not thin slice images based on the thin slice criteria, and transferring or displaying the thin slice series in a different manner than the non-thin slice series, such that either the images of the thin slice series are selectively not transferred, selectively transferred with lower priority, selectively transferred but not displayed, or selectively transferred but otherwise displayed or processed in a selectively different manner.

In one embodiment, a tangible computer readable medium has instructions stored thereon, wherein the instructions are configured for reading by a computing device in order to cause the computing device to perform operations comprising accessing transfer rules associated with a first computing device and a first user, the transfer rules indicating thin slice criteria for determining whether respective medical images of an image series are classified as thin slice images, wherein the thin slice criteria include at least one of a maximum thickness of a particular medical image for classification of the particular image as a thin slice image or a maximum quantity of medical images in the image series for classification of the medical images of the image series as thin slice images, selecting a first group of medical images of an image series that are not thin slices as indicated by the thin slice criteria, and initiating transfer of the first group of medical images to the first viewing environment, wherein medical images of the image series that are not in the first group are not transferred to the first viewing environment.

In one embodiment, a method comprises by a computing device configured for displaying medical images, determining a storage location of a dataset, determining an availability of a processing server to process the dataset, in response to determining that the dataset is locally available to a processing server configured to process the dataset, requesting processing of the dataset by the processing server and accessing the processed dataset from the processing server, and in response to determining that the dataset is not locally available to the processing server and/or the processing server is not available to process the dataset, requesting transmission of at least some of the dataset to the computing device and processing at least some of the dataset at the computing device.

According to an embodiment, a computer-implemented method of rendering medical images is disclosed comprising: by one or more processors executing program instructions: accessing a set of medical image data; analyzing the set of medical image data to determine a value of an attribute of the set of medical image data; accessing a user-defined rule indicating an association between the value of the attribute and a desired image slice thickness; and applying the rule to the set of medical image data to render a series of medical images, wherein medical images of the series match the desired slice thickness.

According to an aspect, the method further comprises: by the one or more processors executing program instructions: automatically initiating display of the series of medical images at a computing device.

According to another aspect, the set of medical image data comprises an original series of medical images, and wherein the medical images comprise two-dimensional medical images.

According to yet another aspect, applying the rule comprises: by the one or more processors executing program instructions: accessing a three-dimensional set of medical image data from which the original series was derived; and rendering the series of medical images from the three-dimensional set of medical image data.

According to another aspect, applying the rule further comprises: by the one or more processors executing program instructions: selecting a group of medical images of the original series of medical images, wherein each medical image of the group of medical images has an image slice thickness greater or less than the desired image slice thickness; and reformatting each of the medical images of the group of medical images to have the desired image slice thickness.

According to yet another aspect, applying the rule further comprises: by the one or more processors executing program instructions: determining that one or more medical images of the original series of medical images has an image slice thickness greater or less than the desired image slice thickness; reformatting the original series of medical images to include a plurality of reformatted medical images having an image slice thicknesses matching the desired image slice thickness, wherein the original series of medical images is reformatted from a volumetric data set associated with the original series of medical images; and initiating display of the original series of medical images including the plurality of reformatted medical images at a computing device.

According to another aspect, the set of medical image data comprises three-dimensional medical image data.

According to yet another aspect, the rule further indicates an association between the value of the attribute and a desired image slice increment, and wherein applying the rule comprises: by the one or more processors executing program instructions: rendering the series of medical images from the three-dimensional set of medical image data, wherein the medical images of the series match both the desired slice thickness and the desired slice increment.

According to another aspect, applying the rule comprises: by the one or more processors executing program instructions: generating each successive image slice of the series from the three-dimensional set of medical image data, where each successive image slice has the desired image thickness and is the desired image slice increment apart.

According to yet another aspect, the method further comprises: by the one or more processors executing program instructions: automatically initiating display of the series of medical images at a computing device.

According to another aspect, the value of the attribute is derived from a DICOM header file.

According to yet another aspect, the attribute comprises at least one of: an image series view, a patient's age, a medical history, a risk factor, a tissue characteristic, or a modality.

According to another aspect, the method further comprises: by the one or more processors executing program instructions: receiving a request from a user to view the series of medical images; and accessing the user-defined rule associated with the user.

According to yet another aspect, the method further comprises: by the one or more processors executing program instructions: displaying the series of medical images on a computing device; receiving a reformat request indicating a new desired image slice thickness different from the desired image slice thickness indicated by the rule; and in response to receiving the reformat request: re-rendering the set of medical image data to generate a new series of medical images, wherein medical images of the new series match the new desired slice thickness.

According to another embodiment, a system is disclosed comprising: a computer readable storage medium having program instructions embodied therewith; and one or more processors configured to execute the program instructions to cause the one or more processors to: access a set of medical image data; analyze the set of medical image data to determine a value of an attribute of the set of medical image data; access a user-defined rule indicating an association between the value of the attribute and a desired image slice thickness; and apply the rule to the set of medical image data to render a series of medical images, wherein medical images of the series match the desired slice thickness.

According to an aspect, the set of medical image data comprises three-dimensional medical image data, and wherein the one or more processors are configured to execute the program instructions to further cause the one or more processors to: render the series of medical images from the three-dimensional set of medical image data, wherein the medical images of the series match both the desired slice thickness and the desired slice increment.

According to another aspect, the one or more processors are configured to execute the program instructions to further cause the one or more processors to: receive a request from a user to view the series of medical images; access the user-defined rule associated with the user; display the series of medical images on a computing device; receive a reformat request indicating a new desired image slice thickness different from the desired image slice thickness indicated by the rule; and in response to receiving the reformat request: re-render the set of medical image data to generate a new series of medical images, wherein medical images of the new series match the new desired slice thickness.

According to yet another embodiment, a computer program product is disclosed comprising a computer readable storage medium having program instructions embodied therewith, the program instructions executable by one or more processors to cause the one or more processors to: access a set of medical image data; analyze the set of medical image data to determine a value of an attribute of the set of medical image data; access a user-defined rule indicating an association between the value of the attribute and a desired image slice thickness; and apply the rule to the set of medical image data to render a series of medical images, wherein medical images of the series match the desired slice thickness.

According to an aspect, the program instructions are executable by one or more processors to further cause the one or more processors to: render the series of medical images from the three-dimensional set of medical image data, wherein the medical images of the series match both the desired slice thickness and the desired slice increment.

According to another aspect, the program instructions are executable by one or more processors to further cause the one or more processors to: receive a request from a user to view the series of medical images; access the user-defined rule associated with the user; display the series of medical images on a computing device; receive a reformat request indicating a new desired image slice thickness different from the desired image slice thickness indicated by the rule; and in response to receiving the reformat request: re-render the set of medical image data to generate a new series of medical images, wherein medical images of the new series match the new desired slice thickness.

According to another embodiment, a system configured to analyze and display medical images is disclosed comprising: a computer readable storage medium having program instructions embodied therewith; and one or more processors configured to execute the program instructions to cause the one or more processors to: access a series of medical images; analyze the series of medical images to determine a value of an attribute of the series of medical images, wherein the attribute comprises an image plane; access a user-defined rule indicating an association between the value of the attribute and a desired display preference; and apply the rule to the series of medical images to cause display of the series of medical images according to the desired display preference.

According to an aspect, the desired display preference includes at least one of: an image rendering process, an image slice thickness, an image slice increment, a field of view, a window, a level, or a color setting.

According to another aspect, the value of the attribute is derived from a DICOM header file.

According to yet another aspect, the attribute further comprises at least one of: an image series view, a patient's age, a medical history, a risk factor, a tissue characteristic, or a modality.

According to another aspect, applying the rule to the series of medical images comprises: rendering the series of medical images according to a user-defined rule associated with the value of the attribute.

According to yet another aspect, the rule indicates a desired slice thickness.

According to another aspect, the one or more processors are configured to execute the program instructions to further cause the one or more processors to: identify a previously displayed series of medical images having the attribute with a second value that matches the value associated with the series of medical images; determine one or more display parameters associated with display of the previously displayed series of medical images; and designating the one or more display parameters as the desired display preference.

According to yet another aspect, identifying a previously displayed series of medical images comprises: by the one or more processors executing program instructions: determining that the previously displayed series of medical images was previously displayed to a same user that the series of medical images are to be displayed to.

According to yet another embodiment, a computer-implemented method of analyzing and displaying medical images is disclosed comprising: by one or more processors executing program instructions: accessing a series of medical images; analyzing the series of medical images to determine a value of an attribute of the series of medical images, wherein the attribute comprises an image plane; accessing a user-defined rule indicating an association between the value of the attribute and a desired display preference; and applying the rule to the series of medical images to cause display of the series of medical images according to the desired display preference.

According to an aspect, the desired display preference includes at least one of: an image rendering process, an image slice thickness, an image slice increment, a field of view, a window, a level, or a color setting.

According to another aspect, the value of the attribute is derived from a DICOM header file.

According to yet another aspect, the attribute further comprises at least one of: an image series view, a patient's age, a medical history, a risk factor, a tissue characteristic, or a modality.

According to another aspect, applying the rule to the series of medical images comprises: by the one or more processors executing program instructions: rendering the series of medical images according to a user-defined rule associated with the value of the attribute.

According to yet another aspect, the rule indicates a desired slice thickness.

According to another embodiment, a computer-implemented method of analyzing and displaying medical images is disclosed comprising: by one or more processors executing program instructions: accessing a series of medical images; analyzing the series of medical images to determine a first value of an attribute of the series of medical images; identifying a previously displayed series of medical images having the attribute with a second value that matches the first value; determining one or more display parameters associated with display of the previously displayed series of medical images; and applying the one or more display parameters to the series of medical images to cause display of the series of medical images according to the one or more display parameters.

According to an aspect, identifying a previously displayed series of medical images comprises: by the one or more processors executing program instructions: determining that the previously displayed series of medical images was previously displayed to a same user that the series of medical images are to be displayed to.

According to another aspect, the series of medical images are automatically initially displayed to the user according to the one or more display parameters.

According to yet another embodiment, a computer-implemented method of automated analysis of medical images is disclosed comprising: by one or more processors executing program instructions: accessing a set of medical image data; automatically analyzing the set of medical image data by a CAP action to determine a value of an attribute of the set of medical image data; accessing a user-defined rule indicating an association between the value of the attribute and a desired image slice thickness; and applying the rule to the set of medical image data to render a series of medical images, wherein medical images of the series match the desired slice thickness.

According to an aspect, the method further comprises: by one or more processors executing program instructions: accessing a plurality of user-defined CAP rules; identifying a CAP rule associated with the set of medical imaging data; and determining the CAP action indicated by the rule.

According to another aspect, the CAP rule is associated with the set of medical imaging data based on at least one of: a modality, an anatomical region, or a medical indicator.

According to yet another aspect, the attribute comprises at least one of: a tissue density, or a presence of an abnormality or a suspected abnormality.

According to another aspect, the method further comprises: by one or more processors executing program instructions: identifying a possible abnormality based on the analyzing of the set of medical image data by the CAP action; and fusing a group of medical images from the series of medical images in a region associated with the possible abnormality.

According to yet another aspect, the method further comprises: by the one or more processors executing program instructions: automatically initiating display of the group of medical images of the series of medical images at a computing device.

According to another aspect, the method further comprises: by one or more processors executing program instructions: determining a rendering location for rendering the series of medical images based on a second user-defined rule.

According to yet another aspect, the second user-defined rule indicates at least one of: a user associated with the user-defined rule, a location at which the series of medical images are to be displayed, or a characteristic of a device upon which the series of medical images to be displayed.

According to another embodiment, a system is disclosed comprising: a computer readable storage medium having program instructions embodied therewith; and one or more processors configured to execute the program instructions to cause the one or more processors to: access a set of medical image data; automatically analyze the set of medical image data by a CAP action to determine a value of an attribute of the set of medical image data; access a user-defined rule indicating an association between the value of the attribute and a desired image slice thickness; and apply the rule to the set of medical image data to render a series of medical images, wherein medical images of the series match the desired slice thickness.

According to an aspect, the one or more processors are configured to execute the program instructions to further cause the one or more processors to: access a plurality of user-defined CAP rules; identify a CAP rule associated with the set of medical imaging data; and determine the CAP action indicated by the rule.

According to another aspect, the CAP rule is associated with the set of medical imaging data based on at least one of: a modality, an anatomical region, or a medical indicator.

According to yet another aspect, the attribute comprises at least one of: a tissue density, or a presence of an abnormality or a suspected abnormality.

According to another aspect, the one or more processors are configured to execute the program instructions to further cause the one or more processors to: identify a possible abnormality based on the analyzing of the set of medical image data by the CAP action; and fuse a group of medical images from the series of medical images in a region associated with the possible abnormality.

According to yet another aspect, the one or more processors are configured to execute the program instructions to further cause the one or more processors to: automatically initiate display of the group of medical images of the series of medical images at a computing device.

According to another aspect, the one or more processors are configured to execute the program instructions to further cause the one or more processors to: determine a rendering location for rendering the series of medical images based on a second user-defined rule.

According to yet another aspect, the second user-defined rule indicates at least one of: a user associated with the user-defined rule, a location at which the series of medical images are to be displayed, or a characteristic of a device upon which the series of medical images to be displayed.

According to yet another embodiment, a computer program product is disclosed comprising a computer readable storage medium having program instructions embodied therewith, the program instructions executable by one or more processors to cause the one or more processors to: access a set of medical image data; automatically analyze the set of medical image data by a CAP action to determine a value of an attribute of the set of medical image data; access a user-defined rule indicating an association between the value of the attribute and a desired image slice thickness; and apply the rule to the set of medical image data to render a series of medical images, wherein medical images of the series match the desired slice thickness.

According to an aspect, the program instructions are executable by one or more processors to further cause the one or more processors to: access a plurality of user-defined CAP rules; identify a CAP rule associated with the set of medical imaging data; and determine the CAP action indicated by the rule.

According to another aspect, the program instructions are executable by one or more processors to further cause the one or more processors to: identify a possible abnormality based on the analyzing of the set of medical image data by the CAP action; and fuse a group of medical images from the series of medical images in a region associated with the possible abnormality.

According to yet another aspect, the program instructions are executable by one or more processors to further cause the one or more processors to: automatically initiate display of the group of medical images of the series of medical images at a computing device.

Additional embodiments of the disclosure are described below in reference to the appended claims, which may serve as an additional summary of the disclosure.

In various embodiments, systems and/or computer systems are disclosed that comprise a computer readable storage medium having program instructions embodied therewith, and one or more processors configured to execute the program instructions to cause the one or more processors to perform operations comprising one or more aspects of the above- and/or below-described embodiments (including one or more aspects of the appended claims).

In various embodiments, computer-implemented methods are disclosed in which, by one or more processors executing program instructions, one or more aspects of the above- and/or below-described embodiments (including one or more aspects of the appended claims) are implemented and/or performed.

In various embodiments, computer program products comprising a computer readable storage medium are disclosed, wherein the computer readable storage medium has program instructions embodied therewith, the program instructions executable by one or more processors to cause the one or more processors to perform operations comprising one or more aspects of the above- and/or below-described embodiments (including one or more aspects of the appended claims).

BRIEF DESCRIPTION OF THE DRAWINGS

The following drawings and the associated descriptions are provided to illustrate embodiments of the present disclosure and do not limit the scope of the claims. Aspects and many of the attendant advantages of this disclosure will become more readily appreciated as the same become better understood by reference to the following detailed description, when taken in conjunction with the accompanying drawings, wherein:

FIG. 2 illustrates a table of transfer and display rules, including example categories of properties/attributes on which transfer and display rules may be based for a user, site, or other group of viewing devices;

FIGS. 3A, 3B, and 3C illustrate example data structures having transfer and display rules of various types;

FIG. 6 illustrates additional example display rules of the present disclosure;

FIG. 7 is a flowchart illustrating an embodiment of another method of the present disclosure;

FIGS. 8A-8B show tables illustrating additional examples of rules of the present disclosure.

DETAILED DESCRIPTION

Embodiments of the disclosure will now be described with reference to the accompanying figures, wherein like numerals refer to like elements throughout. The terminology used in the description presented herein is not intended to be interpreted in any limited or restrictive manner, simply because it is being utilized in conjunction with a detailed description of certain specific embodiments of the disclosure. Furthermore, embodiments of the disclosure may include several novel features, no single one of which is solely responsible for its desirable attributes or which is essential to practicing the embodiments of the disclosure herein described.

Terms

In order to facilitate an understanding of the systems and methods discussed herein, a number of terms are defined below. The terms defined below, as well as other terms used herein, should be construed broadly to include the provided definitions, the ordinary and customary meaning of the terms, and/or any other implied meaning for the respective terms. Thus, the definitions below do not limit the meaning of these terms, but only provide exemplary definitions.

"User" (also referred to herein as "reviewer" and/or "viewer"), as used herein, includes an individual (or group of individuals) that interfaces with a computing device to, for example, access or view medical images. Users may include, for example, physicians (including, for example, doctors, radiologists, etc.) hospital staff, and/or any other individuals (including persons not medically trained) involved in analysis, annotation, comparison, acquisition, storage, management, or other tasks related to medical images (or any other types of images) as described herein. Any discussion herein of user preferences and/or rules (e.g., display rules and transfer rules) associated with users should be construed to also, or alternatively, include user group preferences (or rules associated with groups of users), site preferences/rules, system preference/rules, and/or default software preferences/rules.

Figure 9:
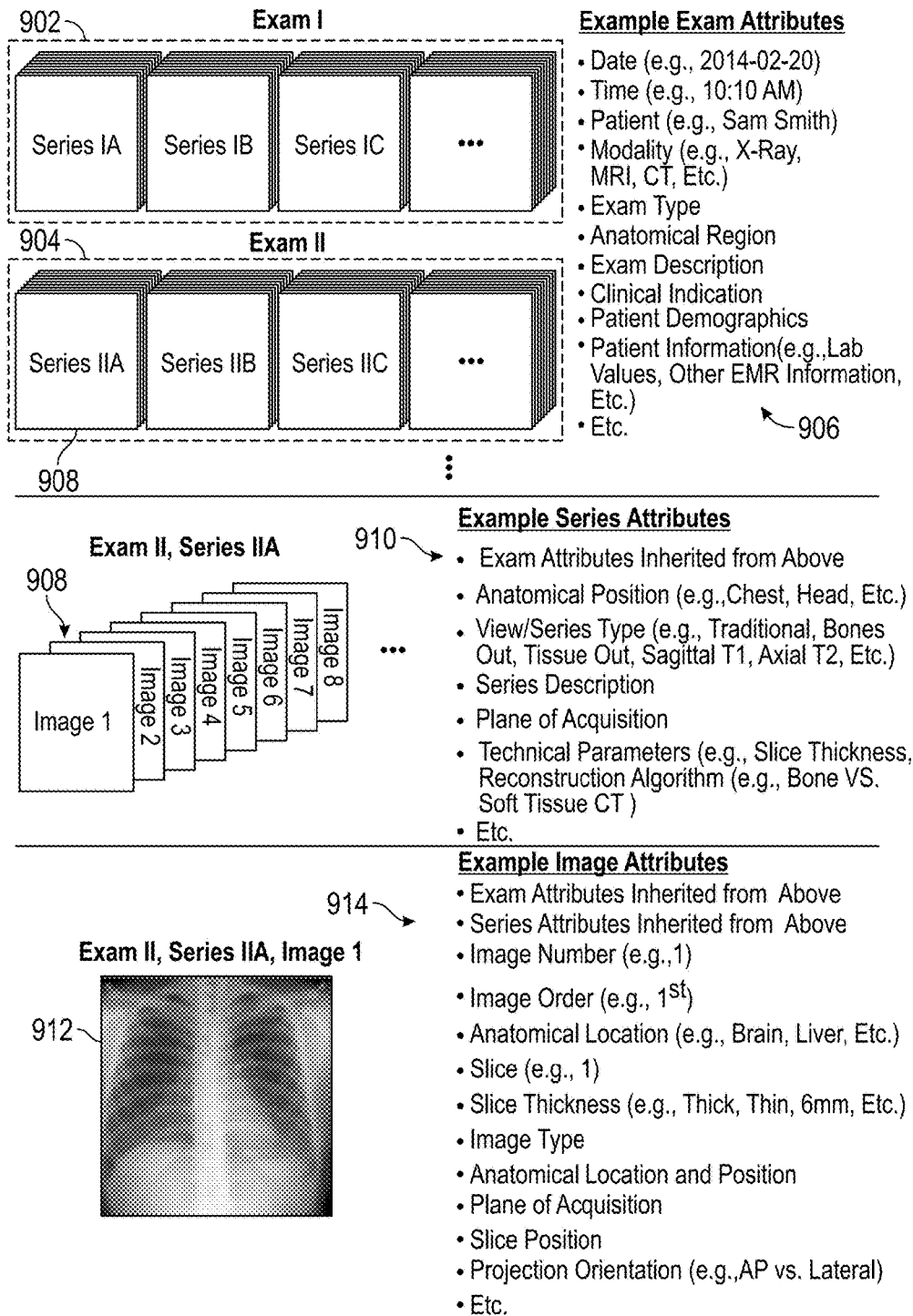
FIG. 9 illustrates various example attributes that may be associated with exams, image series, and images, according to embodiments of the present disclosure.

"Medical data," as used herein, is defined to include any data related to medical information, images, exams, image series, and/or other patient information. As non-limiting examples, medical data may include, but is not limited to, medical images, such as radiograph (e.g., an x-ray image, CR, DR, etc.), computed tomography (CT), magnetic resonance imaging (MRI), Ultrasound (US), mammogram, positron emission tomography scan (PET), nuclear scan (NM), full-field mammography (FFDM) (and other types of digital mammography), Tomosynthesis (e.g., breast tomosynthesis), and images related to gross and microscopic pathology, ophthalmology, endoscopy, or other medical images, as well as medical reports, such as text files containing reports, voice files with results summaries, and/or full digital dictation voice files for transcription. While this description is directed substantially to transmitting and viewing of medical images, the methods and systems described herein may also be used in conjunction with non-medical images, such as, images of circuit boards, airplane wings, and satellite images, for example. Medical images may be reconstructed and/or rendered from 3D or volumetric image data using methods including multiplanar reformation/reconstruction (MPR), maximum intensity projection (MIP), and/or the like (including, e.g., any Computerized Advanced Processing (CAP), as described below). FIG. 9 illustrates an example of a medical image 912 and possible attributes that may be associated with a medical image. The term "medical image data" may be used herein to refer to medical data primarily associated with imaged or imaging data.

"Image series" (also referred to herein as a "series"), as used herein, includes any two or more images that are related. Images in a series typically share one or more common attributes, for example, a type of anatomic plane and/or an image orientation. For example, an image series may comprise two or more images of a particular patient that are acquired on a particular date, e.g., different x-ray projections of the chest. A series of contiguous 3 mm axial CT scans of the chest is another example of an image series. A brain MRI scan might include the following series: sagittal T1 weighted images, axial T1 weighted images, axial FLAIR images, axial T2 weighted images, as well as post contrast axial, sagittal and coronal T1 weighted series. An image series of an exam may be identified by its "type" (also referred to herein as a "series type" and/or a "view type"). For example, series may be acquired using different pulse sequences, acquired in different anatomic planes (also referred to herein as "imaging planes," e.g., axial, coronal, sagittal, etc.), and/or acquired before or after administration of intravenous contrast material. An image series may be limited to images of a certain modality or may comprise images of multiple modalities. FIG. 9 illustrates an example of an image series 908, as well as example attributes that may be associated with an image series. As shown, the image series 908 includes multiple medical images, such as medical image 912.

"Medical imaging exam" (also referred to herein as a "medical exam" and/or an "exam"), as used herein, includes collection of medical data related to an examination of a patient. An exam may be specific to a particular time or time period. Generally, an exam includes one or more medical images and/or image series, montages, reports, notes, graphs, measurements, annotations, videos, sounds or voice data, diagnoses, and/or other related information. An exam may include multiple image series of multiple modalities, volumetric imaging data, reconstructed images and/or rendered images. For example, an exam of a patient may be the brain MRI scan mentioned above, and may include each of the image series obtained on a particular date including: sagittal T1 weighted images, axial T1 weighted images, axial FLAIR images, axial T2 weighted images, as well as post contrast axial, sagittal and coronal T1 weighted series. Another example of an exam may be a dual-energy radiography exam, which may include image data including traditional x-ray image images, bone subtracted (or "bone out") x-ray images, and/or tissue subtracted (or "tissue out") x-ray images. FIG. 9 illustrates two example medical exams 902 and 904. As shown, each medical exam 902 and 904 includes multiple image series, such as image series 908 which is a part of medical exam 904.

"Attributes" (also referred to herein as "properties" and "characteristics"), as used herein, include any characteristics associated with a data item (e.g., a data item such as a medical exam, an image series, a medical image, and/or the like). Attributes may be inherited in a hierarchical manner. For example, a medical image may inherit attributes of an image series of which it is a part, and an image series may inherit attributes of a medical exam of which it is a part. Attributes may be stored as part of an associated data item (e.g., as metadata, Digital Imaging and Communications in Medicine ("DICOM") header data, etc.) and/or separately from an associated data item. FIG. 9 illustrates various example attributes that may be associated with exams (e.g., example attributes 906), image series (e.g., example attributes 910), and images (e.g., example attributes 914). Examples of image attributes include, without limitation, image angle (e.g., an angle of an image with reference to a standard one or more planes of human anatomy; also referred to herein as "scan plane" or "imaging plane"), anatomical position (and/or location) (e.g., a location, with reference to a standard one or more planes of human anatomy, of the patient represented in a particular image), image orientation (e.g., an orientation of the image with reference to a standard one or more planes of human anatomy), image rotation (e.g., a rotation of the image with reference to a standard one or more planes of human anatomy), image field of view, slice thickness, image window and/or level (e.g., a contrast of the image, a brightness of the image, and/or the like), image color map (e.g., that includes information for rendering different pixel intensities as different colors), other color characteristics, image opacity (and/or opacity map), image zoom level, image cropping information, image/series/exam description, whether or not contrast agent was administered, and/or the like. In some instances, one or more image attributes may be user defined and/or based on user preferences/rules. An image attribute may refer to the physical anatomy of a patient from which the image was obtained. For example, a medical image may be obtained to show a particular slice of a patient at a particular location such that a diagnosis of the patient may be made.

"Computerized Advanced Processing" (also referred to herein as "CAP"), as used herein, includes any computerized image analysis, image analysis technique, and/or image processing technique discussed herein, and/or any similar computerized processing technique that is currently available. CAP is described herein with regard to radiology images and other types of medical images, but CAP and the systems and methods described herein may be applied in other areas including, but not limited to, other types of medical images (for example, cardiology, dermatology, pathology and/or endoscopy, among others), computer generated images (for example, 3D images from virtual colonoscopy, 3D images of vessels from CTA, and the like), images from other fields (for example, surveillance imaging, satellite imaging, and the like), as well as non-imaging data including audio, text, and numeric data. In some embodiments, CAP may include, but is not limited to, volume rendering (including, for example, multiplanar reformation/reconstruction (MPR), minimum intensity projection (MinIP), maximum intensity pixel display (MIP), color slabs with various look-up tables (LUTs), full volumes, 3D volume rendering, and/or 3D surface rendering), graphical processing/reporting (e.g., automated identification and outlining of lesions, lumbar discs etc.), automated measurement of lesions or other anatomical features, other computer aided diagnosis (CAD), machine learning-based analysis, artificial intelligence-based analysis, Bayesian analytics, other image processing techniques, and/or the like. Examples of certain types of CAP rules are described below in reference to FIGS. 8A and 8B.

"Slice," "slab," and the like, as used herein, generally refer to medical images obtained, rendered, constructed, reconstructed, etc., from medical imaging data. The term "slab" generally refers to a relatively thick slice. Slices and slabs, and series of slices and slabs, may have any attributes of medical images and series as described herein. For example, a slice may be defined by its thickness (e.g., a thickness of the cross section of imaged tissue). Series of slices may be defined by their anatomical positions, by an increment between each successive slice, by a number slices in the series, etc. For example, in a series of slices, the successive slices may overlap (e.g., contain overlapping medical image data) or not (e.g., in some cases, there may be gaps between the successive slices). In some instances, slices may be combined, or reformatted/re-rendered (e.g., to change the slices' thickness, etc.) by any CAP process and/or in response to a display or transfer rule, as described herein.

The term "thin slices," as used herein, generally refers to any medical images, or related images (e.g., a series of images), having certain slice characteristics/attributes. For example, thin slices may be defined based on a number of slices, e.g., medical images, that are included in an image series. For example, "thin slices" might be defined to include images of any imaging series having more than 200 slices (or any other defined number of slices). Medical images may also, or alternatively, be defined based on a thickness of the cross section of the imaged tissue ("slice thickness") represented in the medical image. For example, "thin slices" might be defined to include images having a slice thickness of less than 1 mm (or any other defined slice thickness). The definition of thin slices may be adjusted based on one or more of many rules or criteria, such as a particular user, site, imaging type, viewing environment (e.g., viewing device characteristic, bandwidth of viewing device) and any number of other related attributes. Thus, thin slices for a particular user at a first site may be defined differently than thin slices for another user at a second viewing site. Similarly, thin slices for a first modality or exam type may be defined differently than thin slices for a second modality or exam type. As described in further detail below, the definition of thin slices and how thin slices (as well as thick slices) are managed (e.g., transferred to various viewing devices) may vary in response to one or more of various attributes associated with the images.

In many medical imaging systems, thin slices, whether defined by a slice thickness and/or slice quantity, are typically stored in order to ensure that the thin slices are later available for use, if necessary. However, in many image viewing applications, some or all of the thin slices may not be necessary to download/view in order to allow the viewer to accurately read an image series. Thus, a viewing system, such as a picture archiving and communication system ("PACS") workstation, may download many thin slices, consuming valuable bandwidth and storage space, where the downloaded thin slices are never viewed by a viewer on the PACS workstation. On the other hand, certain thin slices, such as images associated with particular exam types or modalities, may need to be viewed in order to allow the viewer to accurately read an image series. For example, for certain exams thin slices may need to be reviewed in order to view details that cannot be appreciated in thick slices. Additionally, display environments, e.g., a combination of one or more of a display device, bandwidth, connection speed, availability of thin slices locally, etc., vary widely, such that some display environments might be better suited for viewing and/or downloading a greater quantity of thin slices, while other display environments might be better suited for having a server, such as the PACS server 120 of FIG. 1, render thin slices for viewing via a thin client interface with the display environment, while still other display environments may be better suited to not view or download thin slices at all, even via a thin client interface. Accordingly, the description below describes systems and methods that allow rules to be defined based on one or more of several attributes, such as a particular user, site, or device, as well as whether individual images and/or image series are classified as thin slices, and applied to medical images in order to determine which images are downloaded, viewed, stored, and/or any number of other actions that might be performed with respect to particular images.

"Data store," as used herein, includes any computer readable storage medium and/or device (or collection of data storage mediums and/or devices). Examples of data stores include, but are not limited to, optical disks (e.g., CD-ROM, DVD-ROM, etc.), magnetic disks (e.g., hard disks, floppy disks, etc.), memory circuits (e.g., solid state drives, random-access memory (RAM), etc.), and/or the like. Another example of a data store is a hosted storage environment that includes a collection of physical data storage devices that may be remotely accessible and may be rapidly provisioned as needed (commonly referred to as "cloud" storage).

"Database," as used herein, includes any data structure (and/or combinations of multiple data structures) for storing and/or organizing data, including, but not limited to, relational databases (e.g., Oracle databases, mySQL databases, etc.), non-relational databases (e.g., NoSQL databases, etc.), in-memory databases, spreadsheets, comma separated values (CSV) files, eXtendible markup language (XML) files, TeXT (TXT) files, flat files, spreadsheet files, and/or any other widely used or proprietary format for data storage. Databases are typically stored in one or more data stores. Accordingly, each database referred to herein (e.g., in the description herein and/or the figures of the present application) is to be understood as being stored in one or more data stores.

Example Medical Imaging System

Figure 1A:
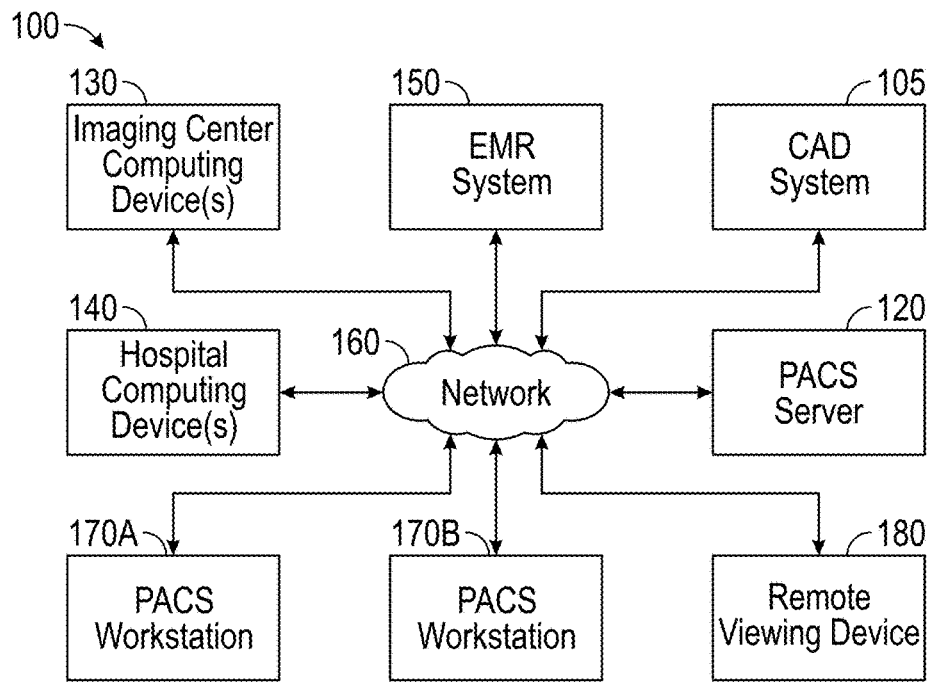
FIG. 1A is a block diagram of an example medical imaging system including two PACS workstations in communication with various devices.
Figure 1B:
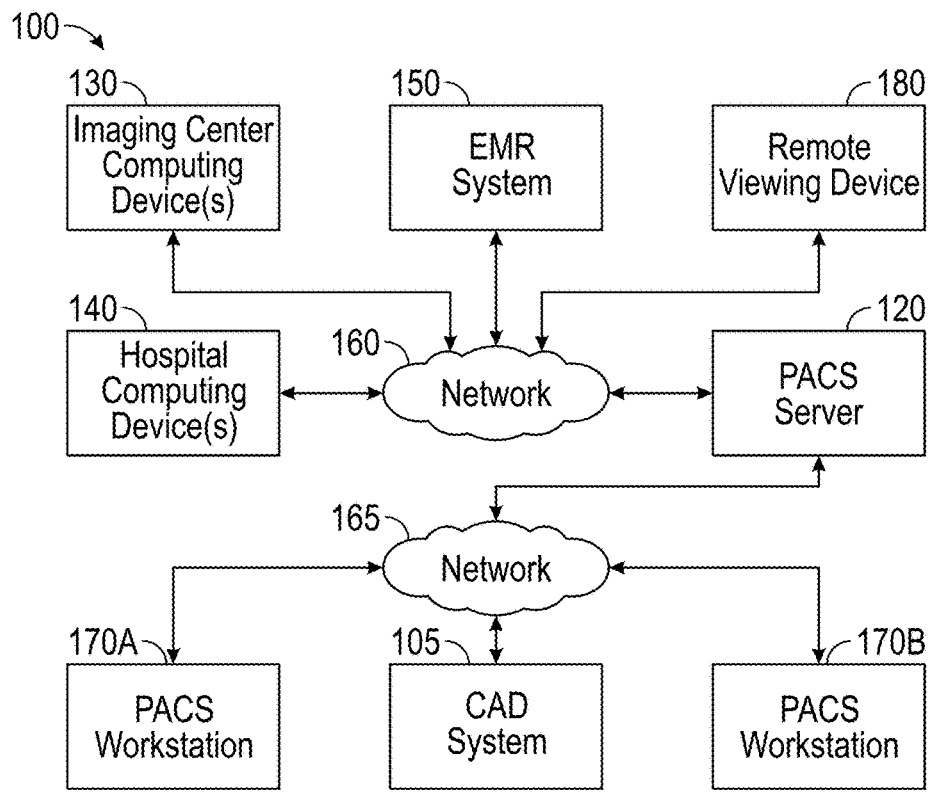
FIG. 1B is a block diagram of an example medical imaging system wherein PACS workstations are in communication with a PACS server via a separate network which may comprise a secured local area network, for example.

FIG. 1A is a block diagram of an example medical imaging system 100 including two PACS workstations 170A and 170B in communication with various devices. The PACS workstations 170A and 170B each include computing systems that are configured to view medical data, such as series of medical images. In the embodiment of FIG. 1A, the PACS workstations 170 and remote viewing device 180 receive medical data, including medical images, via a network 160, which may comprise one or more of any suitable network, such as local area networks (LAN), wide area networks (WAN), personal area networks (PAN), and/or the Internet, for example. In the embodiment of FIG. 1B, the PACS workstations 170 (which includes workstations 170A and 170B) are illustrated in communication with a PACS server 120 via a separate network 165 which may comprise a secured local area network, for example. In either embodiment, the viewing devices, such as the PACS workstations 170 and the remote viewing device 180, are configured to access, download, and/or view medical images. Depending on the embodiment, the viewing devices may each include a special-purpose computing device that is configured especially for viewing medical images or a general purpose computing device, such as a personal computer, that executes software for viewing medical images.

In the embodiment of FIGS. 1A and 1B, a number of entities/devices, including the imaging center computing device(s) 130, the hospital computing device(s) 140, the electronic medical record ("EMR") system 150, and one or more Computer Aided Diagnosis (CAD) systems 105 may generate and/or store medical data, including medical images of varying types, formats, etc., from various imaging devices. The imaging center computing device(s) 130 and the hospital computing device(s) 140 may each include multiple computing devices that are configured to generate, store, and/or transmit medical data, including medical images, to other computing devices, such as the EMR system 150, the PACS server 120, the CAD system 105, and/or any number of processing or viewing devices, such as the PACS workstations 170 and/or remote viewing device 180. The CAD system 105 may generally perform various Computer Aided Processing (CAP) actions as described above and below (e.g., analyzing images, rendering images, re-rendering images, etc.). In an embodiment, the CAD systems functionality may reside within another computing system, e.g., the PACS Server 120, the EMR system 150, or the like.

In accordance with the systems and methods further described below, each of the viewing devices 170 and 180 may be configured to access, download, process and/or view thin slices in a different manner. For example, a user of the PACS workstation 170A may configure his workstation to not download any thin slices to the PACS workstation 170A, where thin slices are defined as images representing a slice thickness of less than 1 mm, while the user of the PACS workstation 170B may also configure his workstation to not download any thin slices, but thin slices are defined as images of an image series having more than 200 images. In various embodiments, as described below, other criteria may be used to determine downloading/transfer/etc. of images. Thus, each of the PACS workstations 170 may download and provide for viewing to viewers different images, such as different images that are classified as thin slices. Similarly, the remote viewing device 180, which is representative of a device that is not dedicated to viewing medical data, such as a home computing device of a doctor (e.g., a radiologist), may define thin slices in a different manner, in consideration of bandwidth and hardware limitations, for example.

In addition to allowing medical image downloading, viewing, processing, and management to be based on their qualifications as thin slices, the systems and methods described herein allow rules for downloading, viewing, processing, storage and/or other management of thin slices, as well as other medical images and types of medical data, based on one or more of a plurality of attributes that are referred to herein as "transfer rules" and/or "display rules." Thus, the transfer and display rules may not only include rules regarding transfer of data (e.g., images, image series, exams, etc.), but may also include rules associated with viewing, processing, storing, printing, and/or otherwise manipulating or managing medical data, such as medical images. Transfer and display rules related to transfer of data may be implemented in a push and/or pull architecture. For example, transfer and display rules may be applied at a device that has local access to the image data for pushing of matching image data to a viewing device or transfer and display rules may be applied at a viewing device for requesting (pulling) matching image data from the device that has local access to the image data.

Depending on the embodiment, transfer and display rules may include criteria based on any attributes of images, series of images, exam descriptions, clinical indications, DICOM information, any other attribute, and/or any combination of attributes. For example, transfer and display rules for transferring medical images to the PACS workstation 170A, may be based on not only whether medical images qualify as thin slices, the transfer and display rules may be based on one or more of client (or viewing device) properties, connection properties, site properties, user properties, exam properties, and/or temporal properties, for example.

As noted above, transfer and display rules may be based on image attributes, as well as series attributes. For example, transfer and display rules may indicate that a first type of image should be transferred, but not a second type of image, even though the two image types might be within the same image series. As one example, in diffusion imaging of the brain, the user might want transfer of the isotropic diffusion images, but not the large number of anisotropic diffusion images that were used to create the isotropic diffusion images on the scanner. Thus, the user might want a rule indicating that anisotropic diffusion images of the brain are not transferred, burned on CD, or printed. Such a rule would not affect the transfer, burning, or printing of isotropic diffusion images, even where the isotropic diffusion images are included in the same image series as anisotropic diffusion images that are affected by the rule. Accordingly, transfer and display rules indicating that isotropic diffusion images are transferred to a particular workstation, but that anisotropic diffusion images in the same series are not transferred to that workstation would not transfer any anisotropic diffusion images of an image series. The type of individual images may be determined in various manners, such as according to attributes in their respective DICOM headers.

Transfer and display rules may also include series-based rules, such as to transfer image series of a particular modality while not transferring image series of other modalities. As another example of series-based transfer rules, consider a CT spine imaging series that includes two series, each 1,000 images×0.5 mm, where the first series is reconstructed in bone algorithm for detection of fractures and the second series is reconstructed in soft tissue algorithm. The viewer might want to routinely transfer the image series in bone algorithm, but not the image series in soft tissue algorithm. The two series may not be distinguishable by number of slices or slice thicknesses, but other information in the DICOM headers of the images in the series (e.g., series description or reconstruction algorithm) may be accessed to determine how and/or when the image series are transferred, viewed, processed, etc.

In another example of series- or image-based rules, images may be transferred, displayed, or otherwise processed, based on imaging plane. For example, transfer and display rules may indicate specific actions to be performed based on whether the images are axial, coronal, sagittal, or any other imaging plane.

In another specific example of transfer and display rules, images may be transferred or otherwise processed based on series attributes as well as series description. For example, a brain CTA might include two large series, a large series of 0.6 mm images of the brain in bone algorithm before contrast and a large series of 0.6 mm images after contrast. The user might want the second images transferred routinely to evaluate the vessels, but not the first series. However, if the clinical history is "trauma" the user might elect to view the first series (bone algorithm) to evaluate for fractures. The two large series have similar slice thickness and image numbers but differ by other criteria, e.g., series description and administration of contrast.

As those of skill in the art will recognize, one reason to transfer certain images is for processing, such as one or more CAP (e.g., 3D volumetric rendering or CAD (computer aided diagnosis)), for example. While transfer and display rules, as used herein, are discussed primarily with reference to display of images and transfers from a server, such as a PACS server 120 to a PACS workstation or other client machine, transfer and display rules may also apply to other types of image processing, such as transfer from a server to other machines, such as in response to viewing of an exam, or portions of the exam, on the PACS workstation. For example, when a viewer displays an exam, the transfer and display rules might cause the thin slices to be transferred to a rendering server, and might involve transfer to more than one place. As a specific example, the rules for a particular viewer (or group of viewers) might be to transfer all image series to the viewer (e.g. to a remote viewing device at the viewer's home or office), including CTA source images that are categorized as thin slices, and to transfer the CTA source images to a 3D rendering server (because the remote viewing device may not be capable of 3D rendering). As another specific example, the rules for a particular viewer (or group of viewers) might be to transfer all image series to the viewer, except the CTA source images that are categorized as thin slices (because the remote viewing device is on a slow network connection), and to transfer the CTA source images to a 3D rendering server for both rendering of the images and viewing the source images in client-server mode.

Because transfer and display rules may be based on such a large range of attributes, transfer and display rules for each user may differ. Similarly, transfer and display rules for combinations of a user with different sites may differ and transfer and display rules for combinations of a user with different viewing devices may differ. Thus, in one embodiment transfer and display rules comprise a set of rules that may vary from one combination of an image, user, site, viewing device, etc., to another combination of an image, user, site, viewing device, etc. Thus, systems and methods described herein provide flexibility in configuring a particular device, one or more devices at a particular site, any device operated by a particular user or class of user, etc., for downloading, viewing, and/or otherwise managing or processing medical images, including thin slices.

The imaging center computing device(s) 130 may include one or more imaging devices of any type, such as imaging devices that are configured to generate MRI, x-ray, mammography, or CT images (or any other type of image, as described above). In one embodiment, image data for certain medical images is stored in DICOM format. The complete DICOM specifications may be found on the National Electrical Manufactures Association Website at <medical.nema.org>. Also, "NEMA PS 3—Digital Imaging and Communications in Medicine," 2004 ed., Global Engineering Documents, Englewood Colo., 2004, provides an overview of the DICOM standard. Each of the above-cited references is hereby incorporated by reference in their entireties.

The example PACS server 120 is configured to store images from multiple sources and in multiple formats, and may be configured to render certain medical images for display on one or more viewing devices via a thin network communication link, for example. For example, the PACS server 120 may be configured to receive medical images in the DICOM format from multiple sources, store these images, and selectively transmit medical images to requesting viewing devices.

The hospital computing device(s) 140 may include and/or be replaced with any other medical facility, such as clinic, doctor's office, or any other medical facility. These medical facilities may each include one or more imaging devices and may share medical images with the PACS server 120 or other authorized computing devices.

Example Display Environments

In one embodiment, each of the PACS workstations 170 and the remote viewing device 180 are configured to download, store, display, and allow user interaction with, medical images. Thus, each of these devices is part of a respective display environment, where the display environment for each device may also include attributes such as a network connection speed, display device characteristics, allotted and/or available storage space, processing speed, and/or other attributes that may affect how medical data is downloaded, stored, and/or viewed by the devices. As used herein, the term "viewing device" refers to a computing system that is used in a display environment, where the viewing devices could include any type of device, such as a smart phone, a tablet computer, a notebook computer, a desktop computer, a server, any other computing device or combination of devices. Thus, each of the PACS workstations 170 and remote viewing device 180 include one or more viewing devices having associated display environments.

Each viewing device includes, for example, one or more computing devices and/or servers that are IBM, Macintosh, Windows, Linux/Unix, or other operating system compatible. In one embodiment, viewing devices each include one or more central processing units ("CPU"), such as conventional or proprietary microprocessors, and one or more application modules that comprise one or more various applications that may be executed by the CPU.

The viewing devices may further include one or more computer readable storage mediums, such as random access memory ("RAM") for temporary storage of information and read only memory ("ROM") for permanent storage of information, and one or more mass storage devices, such as a hard drive, diskette, and/or optical media storage device. Further details regarding the viewing devices, and other computing devices of the present disclosure, are described below.

The viewing devices may include one or more of commonly available input/output (I/O) devices and interfaces, such as a keyboard, mouse, touchpad, and/or printer. In one embodiment, the I/O devices and interfaces for a viewing device may include one or more display devices, such as a monitor, that allows the visual presentation of data, such as medical images and/or other medical data, to a user. More particularly, display devices provide for the presentation of graphical user interfaces ("GUIs"), application software data, and multimedia presentations, for example. In one embodiment, a GUI includes one or more display panes in which medical images may be displayed. According to the systems and methods described below, medical images may be stored on the viewing device or another device that is local or remote, displayed on a display device, and manipulated by one or more application modules. Viewing devices may also include one or more multimedia devices, such as speakers, video cards, graphics accelerators, and microphones, for example.

The viewing devices may include one or more communication interfaces that allow communications with various external devices. For example, the viewing devices of FIG. 1A each may interface with a network 160 that includes one or more of a LAN, WAN, or the Internet, for example. The network 160 may further interface with various computing devices and/or other electronic devices. In the example embodiment of FIG. 1A, the network 160 is coupled to imaging center 130, a hospital 140, an EMR 150, and a PACS server 120, which may each include one or more computing devices. In addition to the devices that are illustrated in FIG. 1, the network 160 may communicate with other computing, imaging, and storage devices.

All computing devices described herein include different combinations of the components described with reference to FIGS. 1A and 1B, as well possibly additional components. For example, a server may include a processor with increased processing power, additional storage devices, but not all of the input/output devices.

The methods described and claimed herein may be performed by any suitable computing device, such as the viewing devices and/or computing devices of imaging centers, hospitals, EMR systems, PACS, and the like.

Rules-Based Approach to Image Processing, Display, Routing and/or Preloading

As noted above, various imaging devices generate medical images having a wide range of attributes/characteristics, such as slice thicknesses and slice quantities included in respective image series. Thus, medical images of various modalities, such as CT, MRI, PET, digital mammography (e.g., breast tomosynthesis), among others, may be processed and/or transferred for display by one or more viewing devices. The medical images may include image series with thin slices, as well as thicker slices, such as thicker axial, coronal, and/or sagittal images, for example. In one embodiment, the thin slices may be stored for occasional use in the near or long term. One or more sets of rules that collectively comprise transfer and display rules may be defined by individual users and/or administrators of entire sites, for example, to define what medical images should be classified as "thin slices," based on image slice thickness and/or the number of images in a series, for example. Depending on the embodiment, the transfer and display rules, which may include thin rules and/or other types of rules, may be stored at any location(s), such as local to a remote viewing device, local to a PACS server, and/or at a network location that is accessible to both remote viewing devices and PACS servers, for example. The transfer and display rules may be stored in any data store, such as in a database or XML file, for example, on any computer readable medium.

The transfer and display rules may allow a user to indicate a preference as to whether thin slices are automatically displayed by default, or if thin slices are only displayed when requested by the user. For example, if an exam includes several image series, including one or more series having thin slices, a site may establish transfer and display rules that control if and how these thin slices are downloaded and/or displayed. Additionally, the transfer and display rules may allow individual users to assign rules that override the site rules. Thus, a first user at a particular display environment may be automatically presented with thin slices based on the transfer and display rules, while a second user at the same display environment is only presented with the thin slices if a specific request to download/view the thin slices is made by the second user, in view of different user rules in the transfer and display rules.

In one embodiment, the transfer and display rules may indicate whether thin slices are transmitted to remote sites, such as the remote viewing device 180 of FIG. 1, based on a variety of criteria, including preferences of the individual user, characteristics of the viewing environment, the user role, available bandwidth, the software client, or many others. For example, a rule might indicate that referring doctors are not presented with thin slices for display by default. Another rule might indicate that for certain users or sites, for example, when media such as a CD or DVD is created and/or when an exam is uploaded to a personal health record ("PHR") or EMR system, for example, the thin slices are not included. Another rule might indicate that when film is printed, the thin slices are not printed.

Rules may also indicate whether thin slices are preloaded into RAM while reading and/or may indicate the priority of preloading. For example, thin slices and/or an entire image series having thin slices might be preloaded into RAM when an exam is displayed, but the thin slices might not actually be displayed, but instead maintained in RAM for immediate access if the user decides to display the thin slice. Other alternatives for transferring, loading into memory, and/or displaying thin slices may also be specified in rules. For example, rules may indicate that (i) thin slices are to be loaded into RAM and displayed after (or while) downloading the images, (ii) the thin slices are loaded into the local memory of the viewing computer and not automatically pre-loaded into RAM or displayed until the user specifies, and/or (iii) thin slices are assigned a lowest priority for use of RAM, such that the thin slices are loaded into RAM only after the other non-thin images of an exam are loaded. Thus, transfer and display rules may include rules that not only relate to movement of images between computing devices, but also within a device, such as whether images are pre-loaded into RAM, the priority of such loading, and whether they are displayed.

Rules may also indicate how and when images are to be displayed, including rules for rendering of images with particular characteristics (e.g., a thickness of images to be displayed).

FIG. 2 illustrates a transfer and display rules table including example categories of properties/attributes on which rules may be based for a user, site, or other group of viewing devices. In the embodiment of FIG. 2, the first two listed properties are slice thickness and number of images in series. As noted above, medical images may be classified as thin slices based on one or both of these first two properties. In some embodiments, transfer and display rules may include only rules used to categorize images as thin slices. However, as indicated in FIG. 2, for example, many other attributes associated with medical images and the viewing environment may be included in the transfer and display rules, such that different viewing environments may not only define thin slices differently, but may interface with thin slices in different manners, based on other transfer and display rules. In some embodiments, the transfer and display rules may also be used as criteria for downloading, viewing, printing, storing, deleting, and/or otherwise managing medical data that match the indicated transfer and display rules. Alternatively, separate sets of criteria, similar to the transfer and display rules, may be established for downloading, viewing, and/or storing medical images, for example.

In the embodiment of FIG. 2, the properties include one or more client properties, such as a client ID that may identify a particular viewing device and/or viewing environment, for example. The client properties may include individual characteristics of a client, such as hardware and/or software capabilities of a particular viewing device. The connection properties may indicate various characteristics of a connection between a viewing device and the Internet, for example, such as a connection speed, type of Internet service, and/or Internet service provider. The site properties may include a site identifier that identifies a particular site, class of sites, or group of sites. The user properties may indicate a particular user, such as by a user ID, username, or the like, as well as a user role, user access rights, user preferences, etc.

In one embodiment, site rules may indicate a default definition for thin slices, as well as rules for how thin slices are downloaded, viewed, and/or otherwise used by viewing devices associated with the particular site. Similarly, user rules may indicate a user specific, or user group specific, definition for thin slices, as well as user rules for how thin slices are downloaded, viewed, and/or otherwise used by viewing devices which the user is controlling. Thus, in one embodiment the site rules and the user rules may differ and, accordingly, may be reconciled by either overriding conflicting rules with the site rules, the user rules, requesting further input from the user, or applying some other rules for reconciling the conflicting rules.

The data structure of FIG. 2 also indicates that rules might be based on exam properties and/or temporal characteristics. In one embodiment, rules associated with one or more exam properties, such as an exam type, imaging device, referring doctor, imaging center, etc., may be considered in determining whether images are transferred to certain viewing devices. Other rules might indicate that only thin slices having a particular type of compression are to be transferred or viewed by a particular user, client, and/or site, for example. Such rules may be used in a real-time manner by a PACS server, to select a compression type that matches a compression type indicated in a rule so that the corresponding thin slices may be transmitted to the associated viewing devices. Rules may also be based on one or more temporal properties, such as when certain images should be downloaded, viewed, etc., by particular viewing devices, users, sites, etc. For example, a user may define a temporal rule indicating that thin slices, defined by the user and/or site rules, for example, should be downloaded to the user's viewing device only after 7:00 PM on weeknights or on weekend days.

The data structure of FIG. 2 also indicates that rules may be based on various other exam, series, and image attributes. For example, as described above in reference to FIG. 9, images 912, image series 908, and exams 902 and 904 may have associated attributes. "Attributes" may propagate through hierarchy. For example, an exam 904 may include multiple image series 908, and each image series may include multiple images 912. As discussed, one or more attribute associated with an instance of lower orders may inherit attributes associated with an instance of higher order. A user may choose to override the inherited attributes in each order having those attributes. In some embodiments, a user may tailor a rule based on these hierarchical orders/relations of various attributes. For example, a user may specify a rule to require first ten image slices (image attribute) of a patient's head having a sagittal plane (series attributes) from exams taken within last two years (exam attribute) reformatted to 2 mm thickness to be transferred to a hospital computing device 140. Additional examples of transfer and display rules and functionality of the system based on various exam, series, and image attributes are described below.

The data structure of FIG. 2 also indicates that rules may be based on prior exam display attributes. A set of medical data having a certain modality may benefit from sharing/inheriting one or more attributes from a prior exam having the same modality. For example, slice thickness rules from a prior exam may be applied to a later-taken same modality exam and facilitate direct comparison between the two medical data sets. Additional examples of transfer and display rules and functionality of the system based on prior exam display attributes are described below.

As mentioned, rules associated with one or multiple of the attributes/properties indicated in FIGS. 2 and 9, as well as other properties or attributes, may be considered in determining if, when, and/or how, medical images, such as thin slices, are transferred, presented for viewing, viewed, stored, printed, etc. As an example of a combination of rules based on multiple attributes, a first viewer may set user rules indicating a personal preference to have only thick sections of CT scans displayed as a routine while reading, but also wants the thin slices preloaded into RAM and displayed only if the viewer goes into MPR or volume rendering mode. The same user may also set rules indicating that for certain exam types, e.g., CTA's for example, the thin slices are presented for viewing as a default, overriding the user's general preference to have only thick sections of CT scans displayed as a default. The user may also establish rules associated with different sites, such that when the viewer is at home, the same CTA thin slices are not displayed. Such rules may also be defined in terms of connection properties, such that if the home viewing device does not meet a particular minimum access speed, the thin slices are not downloaded to the viewing device or the thin slices are downloaded to the viewing device in the background, or the thin slices are downloaded only at certain days of the week and/or times, for example. Thus, the user rules that comprise transfer and display rules may include various attributes and may be combined in various manners to produce robust and precisely customizable rules for transferring, viewing, and managing medical images.

Example Rules

FIGS. 3A, 3B, 3C illustrate example data structures having rules of varying types that may be included as part of transfer and display rules. The transfer and display rules described in reference to FIGS. 3A, 3B, and 3C, and other rules as described below (e.g., in reference to FIGS. 6, 8A, and 8B) may be stored in one or more databases of the system (e.g., on the PACS server 120, the CAD system 105, the EMR system 150, any other systems shown in FIGS. 1A and 1B, or any combination of the above). As discussed above, transfer and display rules may vary depending on many attributes of a medical image or image series, as well as the respective viewing device to which the medical image might be transferred. For example, transfer and display rules for a particular medical image might classify the medical image as a thin slice based on site rules of a first viewing device, while the same medical image is classified as a thick slice based on site rules of a second viewing device. Accordingly, the eventual transfer, viewing, and/or management of the medical image (or lack thereof) by the first and second viewing devices may be quite different. While the data structures of FIGS. 3A, 3B, and 3C illustrate certain rules that may be included in transfer and display rules, rules based on any other attributes may also be included in other systems. Likewise, transfer and display rules may include fewer rules and/or types of rules than is illustrated in the data structures of FIGS. 3A, 3B, and 3C. Additionally, the transfer and display rules may include more specific criteria for a particular type of rule than is illustrated in FIGS. 3A, 3B, and 3C. The example of FIGS. 3A, 3B, and 3C is not intended as limiting the scope of rules or attributes on which transfer criteria may be based, but rather is provided as one example of such transfer and display rules.

FIGS. 3A and 3B illustrate a sample data structure including user-specific rules. In this embodiment, the user establishes different rules for each of two locations associated with the user (home and hospital). In particular, section 310 of the data structure of FIG. 3A includes rules that are specific to a viewing device at the user's home (but could be applied to various other locations or other criteria). For example, a user may specify an orientational preference of the image (e.g., field-of-view and W/L ratio) and/or dimensions of each image (e.g., slice thickness and increment among the slices). Further, a user may specify, in a client-server type of setting, where image processing should occur and where the resulting rendered images should be stored.

However, while a user may specify various aspects of the user's viewing experience with rules by adjusting wide variety of parameters, some rules may conflict with other rules when strictly followed. For example, a user may have specified a rule to display an axial view of an exam when a patient is diagnosed with breast cancer and another rule to display a sagittal view when a patient has a history of spinal injury. When processing a patient who has both conditions, the system may reconcile the such conflicting rules. For example, some embodiments may evaluate the rules in a sequential order and allow, generally, a later evaluated rule to override a prior conflicting rule or vice versa. In some embodiments, rule reconciliation may be based on a hierarchy of rights or user specified exceptions.

The rules associated with the user's home also include exceptions for a particular image type, specifically, a CT image type in this embodiment. Thus, the user has established rules that define how images are classified as thin slices, and further has defined how the thin slices should be managed by the user's home viewing device, with a particular set of rules for only CT images.

As shown in FIG. 3B, the user may also establish rules in section 320 that are specific to a viewing device used by the user at a hospital location. Thus, the viewing devices of the user at the home and hospital locations may receive different sets of the same medical images. It should be apparent to a person skilled in the art that having "exceptions" providing for differentiation based on access location type gives the user a great flexibility. The user may specify any set of rules to configure the system to cater to the user's needs. For example, a user may specify a rule that diagnoses an abnormality (CAD), and when an abnormality is detected, automatically transfers only the image set containing the abnormality (transfer rule) to a second authorized user who can give a second opinion. The second user may have the user's viewing device configured such that it runs one or more coloring CAPs to enhance the images, and reformat the slice thickness (display rule) automatically before the user opens the images.

FIG. 3C illustrates a sample data structure including site rules, such as those that are developed by an administrator of a particular medical imaging center, doctors office, hospital, or other site that views and/or receives medical images. In one embodiment, site rules may be used as default rules for all viewing systems and/or users at or associated with the site. In the embodiment of FIG. 3C, the site rules indicate which rules can be overridden by user rules such as those in FIGS. 3A and 3B. In other embodiments, the site rules may be configured to always override conflicting user rules or the site rules may be configured to always be overridden by user rules. In other embodiments, other rules are used for reconciling conflicting site rules and user rules. As also noted above, rules based on various other attributes may be established by users of the system, and similar reconciliation schemes or rules may be used to determine the proper transfer and display rules for a given image or image series.

Additional examples of transfer and display rules such as those of FIGS. 3A, 3B, and 3C, and associated functionality of the system, are described below.

Reconciliation of Rules

Figure 4:
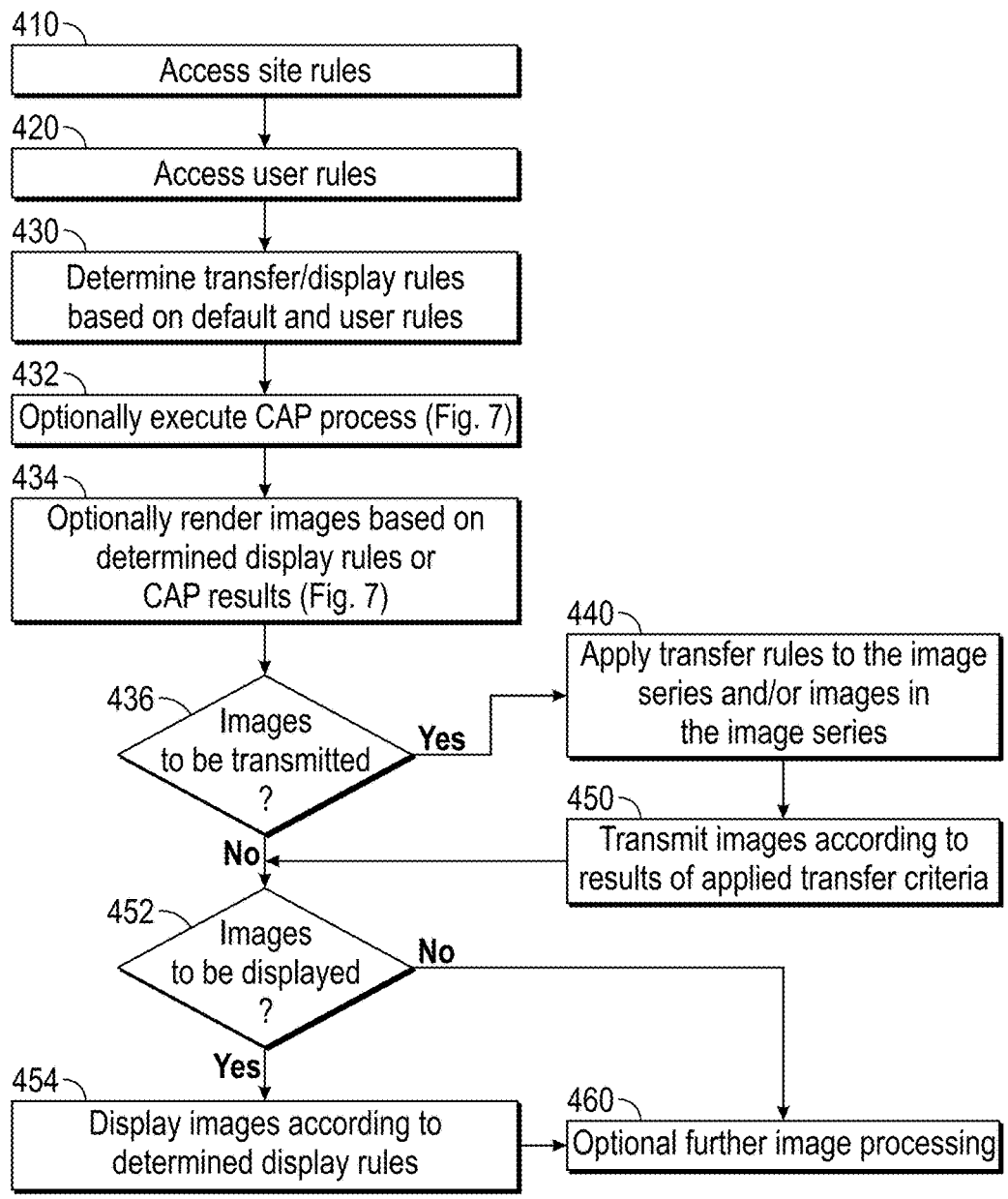
FIG. 4 is a flowchart illustrating an embodiment of a method of the present disclosure.

FIG. 4 is a flowchart illustrating an embodiment of a method of the present disclosure, including, e.g., executing rules and CAP processes, rendering images/series, transmitting and displaying images, and various other functionality related to transfer and display rules such as reconciling default, such as site rules, with user rules.

In one embodiment, various sets of rules, such as site rules and user rules, that are associated with a particular medical image or series of medical images, are reconciled in order to determine a set of transfer and display rules associated with the particular medical image and viewing environment. Thus, the transfer and display rules that are applied to a particular medical image may vary depending on rules associated with one or more of the viewing environment, the viewer, the site, the connection, and/or the client, for example. In one embodiment, the method of FIG. 4 is performed by a device that stores the medical images, such as the PACS server 120 or EMR system 150 of FIGS. 1A and 1B. Depending on embodiment, the method of FIG. 4 may include fewer or additional blocks and blocks may be performed in a different order than is illustrated. In addition, similar methods may be performed in order to determine other functionality with respect to medical images, such as whether medical images should be displayed, stored, printed, etc., based on the determined transfer and display rules. Software code configured for execution on a computing device in order to perform the method of FIG. 4 may be provided on a computer readable medium, such as a compact disc, digital video disc, flash drive, or any other tangible medium. Such software code may be stored, partially or fully, on a memory device of the computing device in order to perform the method outlined in FIG. 4 by those respective devices.

Beginning at blocks 410 and 420, default rules, such as site rules and user rules are accessed. As indicated in FIGS. 3A, 3B, and 3C, site rules and user rules may differ in various ways, including in both defining what medical images should be classified as thin slices and in determining how thin slices and/or thick slices should be treated in view of multiple possible attributes. At block 430, transfer and/or display rules based on the default/user/site/etc. rules are determined. As noted above, the default and/or user rules may include rules defining required or excluded properties of many types, such as properties of the viewing environment, the viewer, the sights, the connection, the exam, and/or the client, for example. The computing device that performs the method of FIG. 4 reconciles the various default/user/site/etc. rules in order to determine transfer and display rules for a particular image or image series (or other set of medical data). Following the rule reconciliation, at block 432, the default/user/site/etc. rules may include an optional block to execute one or more CAP processes. Examples of executing CAP processes are described below in reference to FIG. 7 and other figures. At block 434, the system may optionally render images based on determined display rules or the results of block 432. For example, a user may have defined a rule in which a calcification detection algorithm is executed at block 432 and an associated rule that renders the images with thicker slices is executed at block 434. Further examples of rendering images in response to CAP processes and various rules are described in reference to various figures below.

Next, at block 436, the system determines, based on one or more transfer and display rules, whether to transmit the images (e.g., rendered images) to one or more computing devices. If so, the system applies the transfer rules to the image series and/or images in the image series at block 440. At block 440, the determined transfer rules are applied to the image and/or image series in order to determine how the images should be transferred, and/or stored, if at all, to one or more receiving devices (e.g., a device that is scheduled to receive the particular image series or a device that requests image series). At block 450, medical images, such as thin and thick slices that meet the transfer rules, are transferred to the viewing device.

At block 452, the system determines whether to display the rendered images, e.g., based on one or more display rules. If so, then at block 454 the system applies the display rules to the image and/or image series in order to determine how the images should be displayed by one or more viewing devices. Display of images according to display rules is described in further detail below.

Finally, at block 460, additional optional image processing may optionally be performed by the system, as further described below.

Smart Switching

In certain medical imaging systems, one or both of user-side and server side applications operate upon a similar dataset of information, such as a dataset representing a series of medical images encompassing a volume of tissue. Such applications may be configured to render medical images from the dataset, for example, such as by using advanced processing of cross-sectional medical image series. However, if only a rendering server-side approach is used, the server typically stores a large number of medical data, including datasets associated with medical images, because the server cannot anticipate what medical data will require such advanced processing. Thus, the costs for such server-side systems may be high. In addition, various simultaneous users may compete for server availability and if the server goes down or becomes unavailable, all users may be adversely affected. Alternatively, if a pure client side approach is employed, when a user needs to process a series of images, the images must first be loaded into the memory of their viewing device (client), which often involves transmission of the datasets to the client from a storing server, which may cause a delay of several seconds to several minutes or more as the dataset is made available to the client application. In addition, a pure client-side approach requires that the application be loaded and maintained on each client.

In one embodiment, certain viewing devices and/or image serving devices, such as a PACS server or EMR system, execute a smart switching software module. A smart switching application may include a client-based software application capable of processing data (in this case, rendering of CT, MRI, PET, Ultrasound, for example, as multiplanar or volume rendered images) and optionally a server-based software application with that capability residing on the same network (e.g., network 160 and/or 165 of FIG. 1A, 1B). In one embodiment, the smart switching module on a viewing device is configured to detect the location of a desired dataset and, if the dataset is available on the rendering server, the processing operation(s) (e.g., rendering of the medical images) occurs there, and the results may be viewed on the viewing device via a thin-client viewer, for example. In this embodiment, if the dataset is not available on the rendering server, the rendering server is not available, is busy, and/or there is no rendering server, the dataset may be processed on (possibly after transmission to) the client-based smart switching module on the viewing device. In one embodiment, smart switching may be performed in response to application of transfer and display rules that are based on any attributes, such as any one or more of the properties listed in FIGS. 3A, 3B, and 3C, for example. In one embodiment, transfer and display rules may include attributes related to a particular user (or group of users) or site (or group of sites), such that transfer and display might be performed differently based on the current user and/or site, for example. Depending on the embodiment, the transfer and display rules may be part of the transfer and display rules or may be a separate rule set.

In some embodiments, a user and/or viewing device may want selected image series transferred to a rendering server as opposed to (or in addition to) transfer to a viewing device. For example, a viewer may want to do side-by-side volume rendering of a patient's abdominal aortic aneurysm by comparing the current exam to one from 2 years ago, but the thin slices from the old exam are not in the cache of the rendering server. Thus, the transfer and display rules may indicate that the images from the 2 year old exam are transferred from a PACS server (that still stores the images) to a rendering server. Similarly, transfer and display rules might specify that thin slices are not transferred to a viewing device, but instead might specify that the series be transferred to a central rendering server for 3D processing. Any other set of transfer and display rules may be used to control transfer of images to a rendering server, one or more viewing devices, and/or other devices. For example, in the case of computer aided diagnosis (CAD), e.g., chest CT for nodules or breast imaging, transfer and display rules might specify that the images be transferred to a processing server (in this case for CAD) as well as the viewing device for viewing.

As an example, consider a CT examination that contains 4 series: one axial series with two hundred 4 mm thick slices, one coronal series with one hundred 3 mm thick slices, one sagittal series with one hundred 3 mm thick sections, and one axial series with sixteen hundred 0.5 mm thick sections. Using an example set of rules for defining thin slices, the axial series may be defined by the individual user or site as "thin" because of a slice thickness criteria of under 1 mm, or because of an image per series rule of >200 images.

As noted above, transfer and display rules may indicate a user's preference to not display the thin series when images are typically viewed for reading, or not display them under only certain reading circumstances such as when the client is running with a slow network connection. Suppose the user is working on a client that has not downloaded the thin slices and decides to perform additional image processing while viewing the exam (e.g., perhaps the user wishes to create oblique slices or volume-rendered images). When the user accesses a tool for such advanced processing, e.g., included in the client smart switching module, the system recognizes that the thin slices are not present locally, determines that the thin slices are on a connected rendering server, and enables the user to access the advanced processing application on the server via a thin client (or other connection type), with the rendering operations performed on the server side. Alternatively, if the smart switching application determines that there is no server-side rendering engine available, the smart switching module determines that the thin slices are available but will need to be downloaded, and may initiate download (and possibly background downloading) of the thin slices. Suppose now that the user is working on a client that has downloaded the thin slices into local memory, and decides to perform additional image processing on the thin slices. The smart switching modules may be configured to determine if there is a networked rendering server with a copy of the thin slices, and if so, initiate the processing operations on the server side immediately, with display on the client via a thin client viewer and, if there is no rendering server, make the locally downloaded thin slices available to the locally resident processing application instead.

Use of one or more smart switching modules may advantageously load-balance activities of clients and servers in a way that can be user defined and based on real-time availability of one or more servers, for example. Such load balancing may allow the rendering server to store fewer exams, while allowing for decreased processing times to process data sets that might normally be processed by a client when the server is available for processing. As noted above, a smart switching system for advanced image processing may be combined with rules of varying types, including rules for defining thin slices. In one embodiment, a smart switching module supports the following workflow: (1) if a rule is set (e.g., a user, site, device, or other rule) to show no thin slices, the thin slices are not displayed under the indicated rule preferences (e.g., site rules may indicate that thin slices are not to be downloaded or viewed at a home location), and only the thick slice images are presented; (2) if a user wants to have an exam automatically loaded in advanced visualization mode (or otherwise processed) by rule or switch to that mode, and the thin slices are available on the rendering server, the thin slices can be rendered by the rendering server with minimal delay (as compared to the delay in rendering that might be experienced if rendered on the client); and/or (3) if a user wants to have an exam automatically loaded in advanced visualization mode by rule or switch to that mode, but the images are not available on any rendering server (e.g., the rendering server(s) are busy, down, not available, or absent entirely), the local client is used to render the thin slices, such as by making the appropriate dataset available to the client processing application in background so that other work can be performed in the meantime.

Rendering Server Cluster or Grid

In some embodiments, a rendering server may comprise a cluster or grid of computing devices. For example, a rendering server may include many computing devices that could serve as rendering servers, dedicated rendering servers, and/or other computing devices that can also serve as a rendering server, such as PACS workstation that renders images in a background process for other viewing devices.

For server side rendering, images may or may not be stored at each rendering device (where there are multiple possible rendering devices). For example, if there are multiple rendering devices capable of serving as a rendering server, it may not be efficient for each of them to have a copy of all the cases that might be subjected to rendering. Rendering may include any type of image generation or modification, such as 3D image rendering, 2D image rendering, adjusting a bit depth of images (e.g., adjusting 12-bit DICOM images into 8-bit JPEG images so they can be displayed in browsers and other light clients), and/or any other image manipulations. For ease of explanation, 3D rendering is discussed herein; however, any discussion of 3D rendering should be construed to also describe any other type of rendering.

In addition to each rendering device not having a copy of all image data, users may desire to render old exams that are not stored by any rendering device, for example to compare to new exams. In both cases, the images to be rendered may be transferred to the rendering device at the time of rendering. In one embodiment, a viewing device queries the group of rendering devices, or a device that load-balances rendering requests, with a request that the "fastest" rendering server provide processing. The "fastest" server might not be the fastest rendering device or least busy rendering device, but the one with the most rapid access to the data. For example, consider a series of imaging centers connected with a WAN, each with its own PACS server and 3D rendering device (could be the same machine). A user at site A might need to perform interactive 3D rendering of an exam at remote site B. While equivalent 3D rendering devices might exist at both site A and site B, the system may utilize the remote rendering server at site B because it has the fastest connection to the data, as the data resides locally at site B. Similarly, if images are stored at one rendering device, but not at others, the system may select the rendering device that already has a copy of the images for rendering, rather than another rendering device that might otherwise be used for the rendering.

In one embodiment, rendering of multiple exams requested by a particular viewer/viewing device might occur on different rendering devices. For example, a viewer may need to render a current exam and an old exam, such as to compare the images of the exams. If the old exam was performed at a hospital and the new exam at an imaging center, where it is also being read, the viewer at the imaging center needs to perform 3D volumetric rendering of the two exams, to assess for growth of an abdominal aortic aneurysm, for example. Rather than requiring rendering of both the current and old exams on a particular rendering device (e.g., at the imaging center), according to the systems and methods described herein, rendering of the old exam might be performed by a first rendering device (e.g., at the hospital where the exam is stored), while the new exam is rendered by a second rendering devices (e.g., a client machine at the imaging center).

Figure 5:
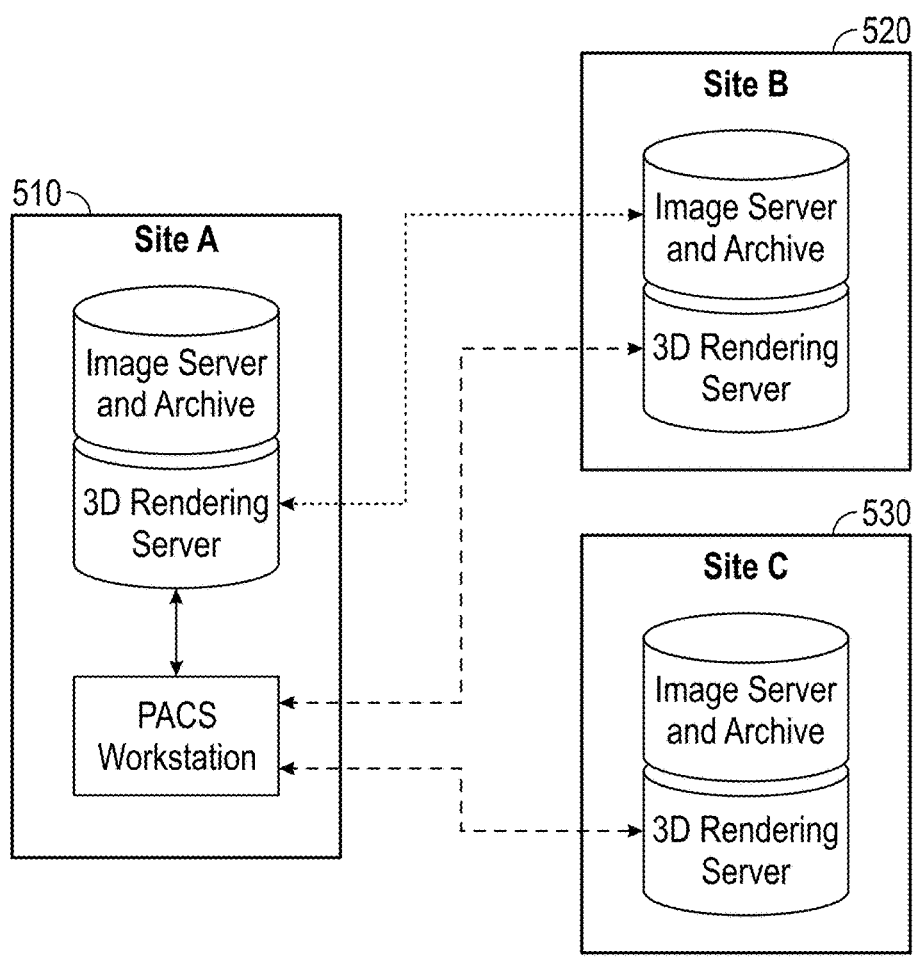
FIG. 5 is a block diagram of three sites that are configured to perform one or more of the operations discussed herein.

FIG. 5 is a block diagram of three sites that are configured to perform one or more of the operations noted above. In particular, FIG. 5 illustrates that site A 510 includes an image server and archive, a 3D rendering server, and a PACS workstation, while each of Sites B 520 and C 530 also include an image server and archive and a 3D rendering server. In one embodiment, the PACS workstation at site A 510 is operated by a viewer (e.g., radiologist or other doctor) in order to view medical images that are rendered by any of the site A, B, or C rendering servers. In other embodiments, the PACS workstation at site A may be replaced by any other viewing device, such as a desktop computer configured to access medical images via a browser or other software, a smart phone, a tablet computer, and/or laptop computer.

In the embodiment of FIG. 5, Site A has requested rendered images that include thin slice images (e.g., either in response to rules that initiate automatic rendering/transfer of the images and/or a request for the rendered images from a user of the PACS workstation at site A 510, for example). However, rather than transferring the large set of thin slice image data from the image server at Site B 520 for rendering by the local rendering server at Site A 510, the workstation A utilizes the rendering server at Site B 520, which has fast local access to the thin slice image data. Thus, processing power at Site A 510 may be used for other purposes while Site B 520 renders the images. Alternatively, if the thin slice image data is stored local to Site A 510, the 3D images may be rendered locally at Site A 510. As discussed above, the rules for defining which device should perform rendering may be based on any number of factors.

In another example, there might be exams that a user at Site A 510 wants to render that are at remote sites B and C, which are connected via slow networks. Thus, one option is to have the exams transferred from these remote sites to the local 3D rendering server at Cite A 510. However, transfer of the image data might be slow. Alternatively, using the smart switching methods described above, the rendering servers at Sites B 520 and Sites C 530 may be automatically utilized to render the images at those remote sites. In one embodiment, such remote rendering may be selected in response to rules, such as a rule that automatically initiates remote rendering of image data for images that are defined as thin slice images and/or based on the bandwidth between the remote rendering servers (e.g., at sites B 520 and C 530).

In one embodiment, images may be rendered at multiple remote rendering devices (e.g., rendering servers at Sites B 520 and C 530) for viewing at a workstation (e.g., PACS workstation at Site A 510). For example, if image data for a first exam of a patient is locally accessible to Site B 520 and image data for a second exam of the patient is locally accessible to Site C 530, and a user of the workstation at Site A 510 wishes to compare rendered images from the first and second exams, images may be rendered by each of the rendering servers at Sites B 520 and C 530 using the respective locally available image data so that Site A 520 may not need to do any image rendering in order to view rendered images of two exams that have been rendered by different remote rendering servers.

Advantageously, distribution of rendering tasks in the manners discussed above may be performed based on rules that initiate rendering by local and/or remote rendering devices, such that the user does not need to manually coordinate rendering of various image data. In various embodiments, images may be rendered via in locations determined based on user-defined rules, CAP results, attributes of a viewing device (e.g., screen resolution, locations of the device), and/or various other factors, as described below.

Examples of Rules-Based Rendering of Medical Images

FIG. 6 illustrates additional example display rules of the present disclosure. With technological advances, some medical imaging which only showed 2D images can now show 3D images or image data, and/or 2D images may be rendered from 3D image data. For example, many ultrasound systems can obtain 3D image data of a fetus, which may be rendered into one or more 2D images. Different users may prefer rendering, transfer, and/or display of 2D slice images (e.g., from 3D medical imaging data) with specific slice thicknesses (and/or other image characteristics). For example, a user may prefer to view image slices with a 3 mm thickness instead of a 0.5-1 mm thickness. Such as preference may be associated with one or more image characteristics. Thus, for example, where an original image set does not have 3 mm thickness, a rendering device may, in response to rules set by the user, reformat the image set having a different thickness and display as if the image set originally had 3 mm thickness. A user may provide one or more display rules to a rendering device, be it a server, client, or in some cases switching between the two, that may retrieve said rules and reformat images based on the retrieved rules.

FIG. 6 provides example display rules having conditions (left column) and associated actions (right column). For example, rule 602 specifies that when a rendering device gets an image set having each slice less than 0.5 mm thick, it will reformat the image set to output a slab having thickness 3 mm. Rules can be flexible and can be defined to trigger on a wide variety of conditions. Some examples of a variety of triggering conditions include triggering when the input image set is associated with a specific plane (e.g., an oblique view condition 608), when an exam property/attribute shows that the patient is a high risk patient (e.g., a patient from a family with history of cancer 610), and/or when an image set has too many slices (e.g., more than thousand slices 612 making it difficult to visually manage).

A rule may have a single condition or have a combined condition (e.g., multiple conditions) that comes into effect only when multiple conditions are concurrently satisfied. Rule 604 is one such rule with a combined condition, in which a condition of exam type being tomography is combined with a condition of each image slice having "thickness less than 0.5 mm." The rule 604 will only come into effect upon encountering an image series that satisfies both criteria before rendering 2 mm slabs. FIG. 6 shows another example of a multiply-defined condition 606 where a patient age is less than 30 years and exam type is tomography. This condition will not trigger the reformat when a patient's age is 31.

The system is not limited to reformatting slices from thin to thick and should not be construed to be limited to offer only unidirectional process. The system is equally capable of reformatting slices from thick to thin (e.g., by generating thin slices from source volumetric/3D data, or source thinner slices, etc.). A default rule may suggest 3 mm thickness slabs but some user rules may prefer to reformat to 1 mm slices.

A display rule for a high risk patient 610 may be one such situation where reformatting to thin slices with small increments may allow the viewer to have a finer inspection of the image data. A user may specify any thickness and increment with rules similar to those shown in FIG. 3A. More specifically, rules 318 and 320 show an embodiment specifying thickness and increment, respectively.

In some embodiments, a user may specify a plurality of rules to be concurrently in effect. For example, the high risk patient rule 610 and number of slices rule 612 can both apply to a same image set. In such situations where multiple rules are concurrently in effect and the command of the rules conflict, a prioritizing scheme that overrides one rule with the other may be implemented. For example, where rules 610 and 612 conflict, the system may give higher priority to prior-defined rule 610 and ignore rule 612, or vice versa. In some embodiments, all triggered rules will run and the last defined rule may override all prior rules' renditions of images. Any outcome determinable rule reconciliation may be adequate.

Some rules may specify "overlap" of slices along with reformatting thickness, as indicated by example display rules 606 and 612. Having overlapping slices may be helpful in providing a viewer with a sense of image continuity and/or allowing the user to perform some CAP to prepare the images for better analysis, such as filtering with moving average filter to remove noise in the image sets. Overlapping slices are a function defined in both slice thickness and increment between the slices. For example, where slice thickness is specified to be 3 mm and increment 4 mm, there will be a 1 mm gap between the slices. Where thickness and increment are specified to be 3 mm, sequential image slices will have neither gaps nor overlaps. Where slices are 3 mm and increment is 2 mm, each slice will have an overlap of 1 mm on each end with an adjacent slice. A user may modify either parameter to reformat images and obtain desired overlaps. It should be apparent to a skilled person in the art that a slice overlap is not limited to one or two slices. For example, a user specifying 0.5 mm thickness and 0.2 mm increment (rules 318 and 320) may get a slice that overlaps with at most 4 other slices.

The rules in FIG. 6 are by no means exclusive and rules bearing on other attributes or display environmental variables are also available. An example of an attribute not specified in FIG. 6 is a "user type" (FIG. 3A gives an example of Radiologist as a value to this attribute). An example of a display environmental variable is network speed. Additionally, transfer and display rules may also take into account other database entries or information in a DICOM header file, such as the patient's age. For example, a user may put forth rules to render slices of a breast tomosynthesis exam progressively thinner based on a patient's age, such as first rule requesting 1.0 mm for 30 years old and above, second rule requesting 0.9 mm for 27 to 30 years old, and third rule requesting 0.8 mm everyone else.

In some examples, rules may incorporate other relevant information that pertains to a patient's risk factors, such as age of the patient or a family history of a particular cancer or other diseases. A user may also create a rule based on other information in the DICOM header, such as view, and specify to render any oblique image data with 4 mm thickness. In some embodiments, these rules may be applied as a default rule to apply to image series. For example, if a rule applied as a default specifies presentation of 3 mm slabs where original images comprise 0.5 mm slices, the system may automatically reformat the 0.5 mm slices to 3 mm slabs.

The system may automatically reformat images following an exam data generation event or in response to user requests (e.g., user sends the system a command equivalent to "read image data"). Referring again to FIG. 4, having reconciled conflicting rules at 430, the system may render image data compliant with predetermined rules at block 434. Here and elsewhere, the term "reformat" is not to be construed narrowly but broadly to include, in a nonlimiting way, a decrease in resolution as well as increase in resolution, applying interpolation algorithms or the like, in addition to already discussed adjustments in slice thickness. Conversion to lower resolution, if not too low so to affect later analyses, may alleviate storage and bandwidth concerns.

In some embodiments, at block 460 of FIG. 4, a user may manually select one or more display rules and request the rendering device to apply the rules. An image set rendered at display block 454 may, in some instances, need to be adjusted by a user, and the system may allow the user to specify and manually apply temporary rules (that may later be saved and become a permanent rule) to reformat images for a more in depth analysis. For example, a user may identify a different complication while viewing an image set with a known abnormality and may want to reformat the image set with a rule that can best show the complication.

It should be noted that the example rules of FIG. 6 are not limited to displaying but should be construed to also include transfer rules. FIG. 6 shows an example rule structure showing what form of conditions and functions various rules may take. Depending on the nature of the action and its conditions, the system may apply a display rule and/or a transfer rule at blocks 432, 434, 440, 454, and/or 460. For example, a rule taking on network speed, data compression, and/or storage space as parameters at block 440 may be a transfer rule. In some embodiments, while a display rule may leave the original image data intact even though it displays a subset of the image data, a transfer rule may cause transmission of only a subset of images. A display rule is unlikely to erase the original after display but a transfer rule may cause an original image to be erased after transfer.

In various embodiments, as illustrated with blocks 614 and 616, rules may take on results of CAP as a condition parameter. CAP actions are described in further detail below in reference to FIG. 7. For example, when the system encounters rules with a condition requiring a CAP result, it executes blocks 702, 704, and/or 706 of the flowchart of FIG. 7 to obtain a result useful for evaluating the outcome of the rule's condition (unless a relevant CAP result is already available from some previous execution of FIG. 7 blocks). See the section on Computer-Aided Analysis and Rendering of Medical Images below for how an independent call to FIG. 7 blocks may be made. With the CAP outcome, rules 614 and 616 may be checked and if satisfied, blocks 708, 710, and 712 of FIG. 7 may be performed at block 434 of FIG. 4.

Examples of Rules-Based Processing and/or Presentation of Medical Images

Advantageously, accordingly to certain embodiments various anomalies may be easily identified in medical images when they are displayed with particular views and thicknesses. Accordingly, the system may allow a user to set rules, based on the modality and the nature of the exam or other attributes, to initially display the image set in a helpful context. For example, a certain user may, through his/her experience with the system, find one configuration to work best and specify one or more rules catered to the user's specific purpose. Referring to FIG. 2, and as discussed herein, transfer and display rules may be based on one or more of exam attributes, series attributes, images attributes (e.g., image plane), prior example display attributes, and/or various other attributes or criteria. Referring to FIG. 3A, example display rules may include specifying particular image planes, Field of View (FOV) 314 and 332, and window and level (W/L) 316. Additional examples are described below and shown in FIGS. 3B and 3C. By defining these types of display rules, a user may, for example, set up a rule for a 3D ultrasound image of a baby to initially display a particular view or image plane, with a particular slice thickness, and with particular window and/or level settings (among other settings).

These rules may provide (by specifying display parameters such as image plane, color, thickness, W/L, FOV, and numerous others) a uniform initial presentation of different image sets (a presentation, here, includes the concept of orientations and is defined to have a broader meaning than an orientation). Where there are many different viewers sharing few viewing devices and each viewing device is frequented by numerous viewers, there are multiple benefits to be had for having user specific presentation of images. Advantageously, according to certain embodiments, the system enables a user to apply display rules for specific orientation, zoom, or performing other transformations to best suit the image to the user's specific needs. It should be noted that these display rules may be applied to transfers and storage as well. In some embodiments, a previous viewer may have closed an image set in a different presentation after viewing, but the system may allow the next viewer to specify a preference of displaying the image set in a familiar presentation. FIGS. 3B and 3C show additional example rules that specify initial presentations defaulting to a user default 326 or to a site default 330. Site rules and user rules may be reconciled at block 430 of FIG. 4 (as described herein), and any optional CAP processes are executed at block 432 of FIG. 4 (as described herein). Then at block 434 of FIG. 4, the system renders an initial image presentation compliant with display rules and optional CAP action (as described herein). Depending on the decision path taken at block 452 of FIG. 4, the system presents the user with the rendered images.

There are other advantages to having rules that configure a presentation. For example, when printing an image set, having a default initial presentation may save the trouble of trying to rematch presentation with prior presentations/displays. The rules do not have to generate an image having one presentation, but may generate many initial images with many pre-defined presentations. For example, when analyzing ultrasound 3D images of a baby, instead of having to re-orient a 3D ultrasound image set for one image of each view, a user may want to define a rule or set of rules which can quickly display, transfer, and/or store one top, one bottom, two sides, and one perspective view.

In some embodiments where an exam image set may be identified as a subsequent image set related to (e.g., related to the same patient, medical diagnosis, image plane, modality, and/or any other attribute) an image set from one or more prior exams, a rendering device may choose display parameters that best mimic display parameters from the prior exams. The display parameters may not be exact, but the rendering device may take a close approximation to present similar presentation between the related exams. A rendering device may retrieve the viewing rules (e.g., slice thickness, plane, or other display parameters), and/or stored state (e.g., brightness or the contrast) of the prior exam's viewing session and apply the rules and the state to the current exam image set. In some embodiments, a user may conveniently switch between similarly presented images from different exams in order to identify any growing abnormalities. In some embodiments, the display parameters may be user-specific, such that only exams previously displayed to the user may be used as a basis for determining display parameters for a new exam displayed to the user.

In some embodiments the display rules may further indicate particular image rendering methods, slice thicknesses, slice increments, and/or the like, based on any image attribute.

Examples of Computer-Aided Analysis and Rendering of Medical Images

In some embodiments, transfer and display rules may take into account one or more CAP (e.g., computer aided diagnoses (CAD)) related to medical images. For example, a CAP action on a mammogram may automatically reveal information on breast density, calcification formation, and/or existence of implants. After the CAP action, for better visual analysis, one or more rules may indicate that a dense breast is to be rendered with thinner slices (or slices or a particular thickness) while images with detected calcification might be rendered with thicker slices (or slices with a particular thickness). Patients with implants might be rendered differently yet.

FIG. 4, as described above, includes blocks related to CAP actions. For example, at blocks 432 and 434 the system may optionally execute one or more CAP actions, and may optionally render images based on display and/or transfer rules related to results of the CAP. Additionally, transfer and/or display rules may indicate CAP-related criteria for display and/or transfer of images, as described herein.

FIG. 7 is a flowchart illustrating an embodiment of the present disclosure related to CAP actions and rendering of images more generally (as may be applicable to various transfer and display rules described above). Blocks 432, 434, 440, 454, and 460 may request FIG. 7 CAP actions, and/or may operate based on results of CAP actions. An example of the flow of FIG. 7 may be understood by reference to example CAP rule/action 810 of FIG. 8. At block 702, the system retrieves the rule (e.g., rule 810) and determines that this rule is to only apply to medical data having modality of MRI and brain exams. The retrieved rule specifies a condition that the exam data (or DICOM header) indicate an existence of a "dementia."

Assuming the condition is satisfied, the rule requests the system to run an MRI Brain Volumetric Analysis at block 704. The system may, in the process, isolate the brain from other matters such as the structure of cranium, and color code the brain to highlight the result. At block 706, the system may then evaluate the CAP result and determine the brain to be significantly smaller than a healthy brain.

In various implementations, as described herein, CAP actions may involve more than simple morphologically based CAD. Rather, CAP action may include, e.g., artificial intelligence and Bayesian analytics as a determining factor in the rendering decision. Such CAP action may be particularly useful in assessing lesion morphology, patient risk factors, and other clinical factors (e.g., in determining the relative suspicion of a breast cancer). Thus, in one example the system may include a rule that indicates that a lesion of is to be rendered in a certain slab thickness, color, window/level, opacity, etc., based on a best depiction of the lesion characteristics that are most associated, e.g., with neoplasm risk (or some other clinical indication determined by a CAP action). Thus, in this example, a lesion that is suspicious (as determined by one or more CAP actions as mentioned herein) may be rendered as a slab of a certain obliquity and thickness to best show, e.g., a branching calcification because the system determined (e.g., by a CAP action) that such a calcification is a likely sign of breast cancer. Furthermore, a user or other system may include a rule that indicates, e.g., "display the images so that the features that most raise suspicion are optimally displayed" or "only adjust the rendering when a lesion is found that has a >2% probability of being neoplastic" or "pre-display a collection of such rendered images that optimally show the most suspicious lesions in an exam in an order based on rank of suspicion."

In various embodiments, blocks 702, 704, and 706 may execute any number of combination of CAP action (the description immediately above providing just one example).

At block 708 the system may determine an image rendering location at block 708.

As discussed in reference to various figures above, including FIG. 5, the rendering of the images may occur in the client side, server side, or any capable computing devices shown in FIGS. 1A and 1B. Generally, images are rendered on a server. However, a higher resolution viewing device may require rendering at a higher resolution so complete rendering on the server followed by a transfer would slow down local rendering. For this reason, if a file is small, it is advantageous to transfer the small file for rendering locally. Also, other image set properties such as number of images to be transferred, bit depth of the images, original file size, and/or rendered file size may be used as criteria in determining whether to transfer an image set or not. Further, any CAPs that consume much computing power or need extensive sets of prior exam data may provide a different rationale in transfer decision making process. For these reasons, a user may prefer to specify one or more rules to supplement Smart Switching mechanism.

Referring to FIGS. 3A and 3B, rules 322, 324, and 328 are examples of user specified location rules. In rule 322, a user has defined that if the user is accessing medical images from home, render images on server. With rule 324, the user has configured the server to store the re-rendered images. Rule 328 is an example of how a user may specify render location based on different access location types. When a user is accessing the medical images at hospital, rule 328 will apply instead of rule 324. Referring again to FIG. 7, after a rendering location is determined, the rendering device will determine relevant rendering parameters from rules, data attributes, and/or environment variables (such as display resolution) at block 710. When ready, the system will render images at block 712.

Referring to FIG. 4, at blocks 440 and 454 some display or transfer rules may be conditioned on results from execution of CAPs. Example rules 614 and 616 of FIG. 6 are of this type. Whenever the necessary CAP result does not yet exist, the system may execute the flow of FIG. 7 from within blocks 440 or 454 of the flowchart of FIG. 4 in order to obtain the CAP result. In tissue density example rule 614, images are to be reformatted/re-rendered to a thickness of 1 mm if the results of a CAP action indicate that tissue density is greater than 5. Advantageously, while the underlying image set may not provide tissue density information by itself, the system may automatically perform a CAP process to determine the tissue density by following the flowchart of FIG. 7. Blocks 702, 704, and 706 calculate tissue density and blocks 708, 710 and 712 may even color-gradient the 3D image based on tissue density. In display rule 614, if CAP result satisfied the tissue density condition, the system will reformat the images to 1 mm at block 454.

Thus, a user's task of scrutinizing image and sorting out a relevant subset of images and making a diagnosis may be greatly sped up and made more accurate as images may be automatically rendered to a thickness that is most beneficial to accurate reading of an exam. As explained above, example rule 614 indicates that the system is to reformat image to 1 mm slices. Such rules may be helpful in detecting abnormalities including breast cancer. For example, women with high breast density may be more likely to get breast cancer than women with low breast density. CAP results (e.g., calculation of breast density) paired with a diagnostic rule (e.g., where tissue density is greater than 5) is a powerful tool that may greatly reduce viewers' time and effort in sifting through irrelevant images. In an embodiment, the system (as directed by one or more rules) may automatically vary image slice thickness (as rendered by the system) based on breast density (or other tissue density). For example, images of dense (or greater than average denseness) tissue (as detected by an automatic CAP action) may be rendered with thinner slice thickness (e.g., a default or base thickness), while images of less dense (or average or lower denseness) tissue (as detected by an automatic CAP action) may be rendered with thicker slices (e.g., the slice thickness may vary between a default value and increase to 10 mm). The opposite may also be true, in another implementation.

The rule 614 only looked at one CAP result—calculated tissue density—and compared it to a scalar value of 5. However, a user may specify more sophisticated rules that employ multiple CAPs. For example, rule 616 has a CAP searching for an abnormality. The CAP in 616 may be any of the CAPs in FIG. 8A, including spine fracture detection, lung nodule detection, lung parenchyma analysis, etc. A user may provide a list of CAPs to run in search for multiple types of abnormalities. For rule 616, when the system finds an abnormality such as a calcified breast, it may then fuse together relevant slices of the image set and return a subset containing only the fused slices. The fused slices might more clearly show the suspected abnormality.

Referring to the flowchart of FIG. 4, at block 460 a user may choose to perform any further and optional image processing. In some embodiments, a user will simply select one or more predefined rules and activate the selected rules. In some embodiments, a user may create a new rule and activate the rule and/or save the rule in a storage device connected to the network. In some embodiments, a user may interactively re-orient, zoom, color, highlight, annotate, comment, or perform any semantically and/or visually enhancing operations. Some of these optional image processing or enhancing operations may utilize CAP.

All of the blocks where CAP can be called may trigger an alert and/or notification for the user. In some embodiments, the alert and/or notification is automatically transmitted to a device operated by the user associated with a corresponding trigger. The alert and/or notification can be transmitted at the time that the alert and/or notification is generated or at some determined time after generation of the alert and/or notification. When received by the device, the alert and/or notification can cause the device to display the alert and/or notification via the activation of an application on the device (e.g., a browser, a mobile application, etc.). For example, receipt of the alert and/or notification may automatically activate an application on the device, such as a messaging application (e.g., SMS or MMS messaging application), a standalone application (e.g., a health data monitoring application or collection management application used by a collection agency), or a browser, for example, and display information included in the alert and/or notification. If the device is offline when the alert and/or notification is transmitted, the application may be automatically activated when the device is online such that the alert and/or notification is displayed. As another example, receipt of the alert and/or notification may cause a browser to open and be redirected to a login page generated by the system so that the user can log in to the system and view the alert and/or notification. Alternatively, the alert and/or notification may include a URL of a webpage (or other online information) associated with the alert and/or notification, such that when the device (e.g., a mobile device) receives the alert, a browser (or other application) is automatically activated and the URL included in the alert and/or notification is accessed via the Internet.

FIG. 8A is a table illustrating additional example rules related to CAP actions that may be performed by the system. For example, various of the rules shown in FIG. 8A may be used to automatically determine one or more CAP to perform on an image, image series, and/or imaging exam. In this example, the table (which may be any other data structure in other embodiments) indicates associations between particular modalities (column 802), exam types (column 804), and CAP (column 806) that may be valuable to examination of the exam images. The table further includes a rules column 808 that includes rules for execution of the CAP indicated in column 806. The rules may indicate that certain CAP are performed automatically (for example, without any input from the doctor), automatically if certain conditions are met (for example, insurance covers, exam has certain characteristics, previous CAP has certain results, and the like), or after confirmation from a radiologist, for example. In the example rules 808, words in quotes indicate clinical indication or history, such as "trauma." The rules may include other criteria for executing one or more CAP, for example based on one or more of:
  Which CAP systems are available
  Exam characteristics, for example, MRI of spine vs. CT of brain
  Clinical information, for example, brain MRI where clinical question is dementia (one type of processing) vs. trauma (another type of processing)
  User preference
  Site preference
  Insurance approval
  Billable status
  Referring docs order
  Presence of comparison exam
  Whether or not a certain type of CAP was already performed on the exam and/or on a prior exam, for example:
    If prior exam used CAD, automatically compare to result.
    If prior exam used Quantitative Analysis, automatically compare to result.
  Results of another CAP. For example, a rule may indicate that a particular CAP should be run if another specific CAP had a certain result (for example, another CAP had a result that was abnormal, normal, demonstrated a particular finding, demonstrated a measurement in a particular range, and/or the like).
  Status of another CAP. For example, a rule may indicate that two CAP should be performed, but that a second CAP should not be performed until the first CAP is complete. By way of example, "Brain aneurysm detection CAD" may require that a "3D Vessel tracking" CAP be run first, as "Brain aneurysm detection CAD" may process the results of "3D Vessel tracking" CAP.

The last example rule listed in the example CAP Rules table of FIG. 8B (described below) illustrates another example in which three CAP are automatically run in a particular sequence in the event that two conditions are met.

In some embodiments certain results of a CAP may automatically trigger the scheduling of another CAP (for example, based on the rules in column 808). For example, the modality and exam in rule 810 is associated with Brain MRI exams (as indicated in columns 802 and 804), and the indicated CAP of "MRI brain volumetric analysis" is associated with a rule (column 808) indicating that the CAP is automatically performed when the clinical indication is "dementia."

In some embodiments, scheduling of a particular CAP, either automatically or manually, may automatically cause one or more other CAP to be scheduled before or after that particular CAP. For example, exam rule 812 indicates that scheduling of "Brain aneurysm detection CAD" should result in the automatic scheduling of "3D Vessel tracking" CAP, and that "3D Vessel tracking" CAP should be run before "Brain aneurysm detection CAD", for example because "Brain aneurysm detection CAD" involves processing the results of "3D Vessel tracking" CAP.

In another example, the modality and exam in rule 811 is associated with Brain MRI exams (as indicated in columns 802 and 804), and the indicated CAP of "MRI brain CSF analysis" is associated with a rule (column 808) indicating that the CAP is automatically performed when the clinical indication is "hydrocephalus" "or if an abnormal brain volumetric analysis resulted from another CAP (e.g., a result of running rule 810 for "Dementia").

Thus, in an embodiment, the first CAP in rule 810 ("MRI Brain volumetric analysis") may first be automatically performed on a brain MRI, such as in response to an indication of "dementia" in the MRI order from the referring doctor. Once the MRI brain volumetric analysis has been performed, the rules of FIG. 8A may again be applied to determine if one or more additional CAP should be performed. In this example, if the result of the MRI brain volumetric analysis is "abnormal" (or equivalent nomenclature), another CAP listed in rule 811 (MRI brain CSF analysis) is triggered for automated execution. Thus, in various embodiments, the rules may be configured to initiate execution of multiple CAP in response to results of previously performed CAP.

In one embodiment, a rules data structure may be used to determine which CAP are compatible and/or available for a particular one or more image series, such as based on various characteristics associated with the one or more image series. For example, a rules data structure comprising modality, exam, and CAD/processing, such as columns 802, 804, and 806 in the example of FIG. 8A, may be used to determine which of the various CAD/processing are compatible with medical images in particular exam modalities and exams. In one embodiment, this information may be presented to users. In the example of rows 810 and 811, "MRI brain volume analysis" and "MRI brain CSF analysis" are listed as compatible and/or available for MRI exams of the brain.

In various embodiments, different rules may apply to different users and/or different user groups (for example, based on preferences of the users and/or user groups). In any of the blocks where CAP rules may be performed, a user may run a CAD. CAD is a type of CAP that returns, in general, a relevant Boolean or probabilistic result to an inquiry regarding an existence of a disease and/or abnormality. The example CAPs 810, 811, and 812 are few examples of CADs. Some CAD rules may, in addition to the relevant Boolean or probabilistic result, also provide an image set (or any other relevant data) for a user to verify and/or further investigate the CAD result. For instance, the example CAP 812 takes in the "3D Vessel Tracking" results, which may contain 3D vessel images of brain, that can be used as the input to "Brain Aneurysm Detection CAD."

FIG. 8B is a table illustrating additional example rules related to CAP actions that may be performed by the system. For example, the rules of FIG. 8B may be used by the system to automatically determine one or more CAP to perform on an image or image series.

In various embodiments, rules related to CAP may be evaluated automatically, for example when:
   An exam is completed on a scanner.
   An exam is communicated, for example, from a scanner to a PACS System or from a PACS System to a PACS Workstation.
   A CAP is performed, for example, such that the result of the CAP may automatically trigger performance of another CAP.

In various embodiments, evaluation of rules related to CAP may be performed on one or more computing devices, such as scanners, PACS Systems, PACS Workstations, and the like. Based on the evaluation of rules related to CAP, one or more CAP may be automatically executed.

Additional Implementation Details and Embodiments

Various embodiments of the present disclosure may be a system, a method, and/or a computer program product at any possible technical detail level of integration. The computer program product may include a computer readable storage medium (or mediums) having computer readable program instructions thereon for causing a processor to carry out aspects of the present disclosure.

For example, the functionality described herein may be performed as software instructions are executed by, and/or in response to software instructions being executed by, one or more hardware processors and/or any other suitable computing devices. The software instructions and/or other executable code may be read from a computer readable storage medium (or mediums).

The computer readable storage medium can be a tangible device that can retain and store data and/or instructions for use by an instruction execution device. The computer readable storage medium may be, for example, but is not limited to, an electronic storage device (including any volatile and/or non-volatile electronic storage devices), a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a solid state drive, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions (as also referred to herein as, for example, "code," "instructions," "module," "application," "software application," and/or the like) for carrying out operations of the present disclosure may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. Computer readable program instructions may be callable from other instructions or from itself, and/or may be invoked in response to detected events or interrupts. Computer readable program instructions configured for execution on computing devices may be provided on a computer readable storage medium, and/or as a digital download (and may be originally stored in a compressed or installable format that requires installation, decompression or decryption prior to execution) that may then be stored on a computer readable storage medium. Such computer readable program instructions may be stored, partially or fully, on a memory device (e.g., a computer readable storage medium) of the executing computing device, for execution by the computing device. The computer readable program instructions may execute entirely on a user's computer (e.g., the executing computing device), partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present disclosure.

Aspects of the present disclosure are described herein with reference to flowchart illustrations and/or block diagrams of methods, apparatus (systems), and computer program products according to embodiments of the disclosure.

It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart(s) and/or block diagram(s) block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks. For example, the instructions may initially be carried on a magnetic disk or solid state drive of a remote computer. The remote computer may load the instructions and/or modules into its dynamic memory and send the instructions over a telephone, cable, or optical line using a modem. A modem local to a server computing system may receive the data on the telephone/cable/optical line and use a converter device including the appropriate circuitry to place the data on a bus. The bus may carry the data to a memory, from which a processor may retrieve and execute the instructions. The instructions received by the memory may optionally be stored on a storage device (e.g., a solid state drive) either before or after execution by the computer processor.

The flowchart and block diagrams in the Figures illustrate the architecture, functionality, and operation of possible implementations of systems, methods, and computer program products according to various embodiments of the present disclosure. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. In addition, certain blocks may be omitted in some implementations. The methods and processes described herein are also not limited to any particular sequence, and the blocks or states relating thereto can be performed in other sequences that are appropriate.

It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions. For example, any of the processes, methods, algorithms, elements, blocks, applications, or other functionality (or portions of functionality) described in the preceding sections may be embodied in, and/or fully or partially automated via, electronic hardware such application-specific processors (e.g., application-specific integrated circuits (ASICs)), programmable processors (e.g., field programmable gate arrays (FPGAs)), application-specific circuitry, and/or the like (any of which may also combine custom hard-wired logic, logic circuits, ASICs, FPGAs, etc. with custom programming/execution of software instructions to accomplish the techniques).

Any of the above-mentioned processors, and/or devices incorporating any of the above-mentioned processors, may be referred to herein as, for example, "computers," "computer devices," "computing devices," "hardware computing devices," "hardware processors," "processing units," and/or the like. Computing devices of the above-embodiments may generally (but not necessarily) be controlled and/or coordinated by operating system software, such as Mac OS, iOS, Android, Chrome OS, Windows OS (e.g., Windows XP, Windows Vista, Windows 7, Windows 8, Windows 10, Windows Server, etc.), Windows CE, Unix, Linux, SunOS, Solaris, Blackberry OS, VxWorks, or other suitable operating systems. In other embodiments, the computing devices may be controlled by a proprietary operating system. Conventional operating systems control and schedule computer processes for execution, perform memory management, provide file system, networking, I/O services, and provide user interface functionality, such as a graphical user interface ("GUI"), among other things.

As described above, in various embodiments certain functionality may be accessible by a user through a web-based viewer (such as a web browser), or other suitable software program. In such implementations, the user interface may be generated by a server computing system and transmitted to a web browser of the user (e.g., running on the user's computing system). Alternatively, data (e.g., user interface data) necessary for generating the user interface may be provided by the server computing system to the browser, where the user interface may be generated (e.g., the user interface data may be executed by a browser accessing a web service and may be configured to render the user interfaces based on the user interface data). The user may then interact with the user interface through the web-browser. User interfaces of certain implementations may be accessible through one or more dedicated software applications. In certain embodiments, one or more of the computing devices and/or systems of the disclosure may include mobile computing devices, and user interfaces may be accessible through such mobile computing devices (for example, smartphones and/or tablets).

Many variations and modifications may be made to the above-described embodiments, the elements of which are to be understood as being among other acceptable examples. All such modifications and variations are intended to be included herein within the scope of this disclosure. The foregoing description details certain embodiments. It will be appreciated, however, that no matter how detailed the foregoing appears in text, the systems and methods can be practiced in many ways. As is also stated above, it should be noted that the use of particular terminology when describing certain features or aspects of the systems and methods should not be taken to imply that the terminology is being re-defined herein to be restricted to including any specific characteristics of the features or aspects of the systems and methods with which that terminology is associated.

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

Conjunctive language such as the phrase "at least one of X, Y, and Z," or "at least one of X, Y, or Z," unless specifically stated otherwise, is to be understood with the context as used in general to convey that an item, term, etc. may be either X, Y, or Z, or a combination thereof. For example, the term "or" is used in its inclusive sense (and not in its exclusive sense) so that when used, for example, to connect a list of elements, the term "or" means one, some, or all of the elements in the list. Thus, such conjunctive language is not generally intended to imply that certain embodiments require at least one of X, at least one of Y, and at least one of Z to each be present.

The term "a" as used herein should be given an inclusive rather than exclusive interpretation. For example, unless specifically noted, the term "a" should not be understood to mean "exactly one" or "one and only one"; instead, the term "a" means "one or more" or "at least one," whether used in the claims or elsewhere in the specification and regardless of uses of quantifiers such as "at least one," "one or more," or "a plurality" elsewhere in the claims or specification.

The term "comprising" as used herein should be given an inclusive rather than exclusive interpretation. For example, a general purpose computer comprising one or more processors should not be interpreted as excluding other computer components, and may possibly include such components as memory, input/output devices, and/or network interfaces, among others.

While the above detailed description has shown, described, and pointed out novel features as applied to various embodiments, it may be understood that various omissions, substitutions, and changes in the form and details of the devices or processes illustrated may be made without departing from the spirit of the disclosure. As may be recognized, certain embodiments of the inventions described herein may be embodied within a form that does not provide all of the features and benefits set forth herein, as some features may be used or practiced separately from others. The scope of certain inventions disclosed herein is indicated by the appended claims rather than by the foregoing description. All changes which come within the meaning and range of equivalency of the claims are to be embraced within their scope.

What is claimed is:

1. A computer-implemented method of automated analysis of medical images, the method comprising:
by one or more processors executing program instructions:
accessing a set of medical image data;
automatically analyzing the set of medical image data by a CAP action to determine a value of an attribute of the set of medical image data;

accessing a user-defined rule indicating an association between the value of the attribute and a desired image slice thickness;

determining whether the set of medical image data is formatted according to the desired image slice thickness indicated by the user-defined rule; and in response to determining that at least a portion of the set of medical image data is not formatted according to the desired image slice thickness rendering at least the portion of the set of medical image data as a series of medical images having the desired slice thickness.

2. The computer-implemented method of claim 1 further comprising:

by one or more processors executing program instructions:

accessing a plurality of user-defined CAP rules;

identifying a CAP rule associated with the set of medical imaging data; and determining the CAP action indicated by the rule.

3. The computer-implemented method of claim 2, wherein the CAP rule is associated with the set of medical imaging data based on at least one of: a modality, an anatomical region, or a medical indicator.

4. The computer-implemented method of claim 2, wherein the attribute comprises at least one of: a tissue density, or a presence of an abnormality or a suspected abnormality.

5. The computer-implemented method of claim 2 further comprising:

by one or more processors executing program instructions:

identifying a possible abnormality based on the analyzing of the set of medical image data by the CAP action; and fusing a group of medical images from the series of medical images in a region associated with the possible abnormality.

6. The computer-implemented method of claim 5 further comprising:

by the one or more processors executing program instructions:

automatically initiating display of the group of medical images of the series of medical images at a computing device.

7. The computer-implemented method of claim 2 further comprising:

by one or more processors executing program instructions:

determining a rendering location for rendering the series of medical images based on a second user-defined rule.

8. The computer-implemented method of claim 7, wherein the second user-defined rule indicates at least one of: a user associated with the user-defined rule, a location at which the series of medical images are to be displayed, or a characteristic of a device upon which the series of medical images to be displayed.

9. A system comprising:

a computer readable storage medium having program instructions embodied therewith; and one or more processors configured to execute the program instructions to cause the one or more processors to:

access a set of medical image data;

automatically analyze the set of medical image data by a CAP action to determine a value of an attribute of the set of medical image data;

access a user-defined rule indicating an association between the value of the attribute and a desired image slice thickness;

determine whether the set of medical image data is formatted according to the desired image slice thickness indicated by the user-defined rule; and in response to determining that at least a portion of the set of medical image data is not formatted according to the desired image slice thickness render at least the portion of the set of medical image data as a series of medical images having the desired slice thickness.

10. The system of claim 9, wherein the one or more processors are configured to execute the program instructions to further cause the one or more processors to:

access a plurality of user-defined CAP rules;

identify a CAP rule associated with the set of medical imaging data; and determine the CAP action indicated by the rule.

11. The system of claim 10, wherein the CAP rule is associated with the set of medical imaging data based on at least one of: a modality, an anatomical region, or a medical indicator.

12. The system of claim 10, wherein the attribute comprises at least one of: a tissue density, or a presence of an abnormality or a suspected abnormality.

13. The system of claim 10, wherein the one or more processors are configured to execute the program instructions to further cause the one or more processors to:

identify a possible abnormality based on the analyzing of the set of medical image data by the CAP action; and fuse a group of medical images from the series of medical images in a region associated with the possible abnormality.

14. The system of claim 13, wherein the one or more processors are configured to execute the program instructions to further cause the one or more processors to:

automatically initiate display of the group of medical images of the series of medical images at a computing device.

15. The system of claim 10, wherein the one or more processors are configured to execute the program instructions to further cause the one or more processors to:

determine a rendering location for rendering the series of medical images based on a second user-defined rule.

16. The system of claim 15, wherein the second user-defined rule indicates at least one of: a user associated with the user-defined rule, a location at which the series of medical images are to be displayed, or a characteristic of a device upon which the series of medical images to be displayed.

17. A computer program product comprising a non-transitory computer readable storage medium having program instructions embodied therewith, the program instructions executable by one or more processors to cause the one or more processors to:

access a set of medical image data;

automatically analyze the set of medical image data by a CAP action to determine a value of an attribute of the set of medical image data;

access a user-defined rule indicating an association between the value of the attribute and a desired image slice thickness;

determine whether the set of medical image data is formatted according to the desired image slice thickness indicated by the user-defined rule; and in response to determining that at least a portion of the set of medical image data is not formatted according to the desired image slice thickness render at least the portion of the set of medical image data as a series of medical images having the desired slice thickness.

18. The computer program product of claim 17, wherein the program instructions are executable by one or more processors to further cause the one or more processors to:
   access a plurality of user-defined CAP rules;
   identify a CAP rule associated with the set of medical imaging data; and
   determine the CAP action indicated by the rule.

19. The computer program product of claim 18, wherein the program instructions are executable by one or more processors to further cause the one or more processors to:
   identify a possible abnormality based on the analyzing of the set of medical image data by the CAP action; and
   fuse a group of medical images from the series of medical images in a region associated with the possible abnormality.

20. The computer program product of claim 19, wherein the program instructions are executable by one or more processors to further cause the one or more processors to:
   automatically initiate display of the group of medical images of the series of medical images at a computing device.

* * * * *